(12) United States Patent
Kelleher et al.

(10) Patent No.: US 8,975,069 B2
(45) Date of Patent: Mar. 10, 2015

(54) METHOD FOR IDENTIFYING ANTIGEN-SPECIFIC REGULATORY T CELLS

(75) Inventors: Anthony Dominic Kelleher, Bangor (AU); John James Zaunders, Kingsford (AU); Nabila Seddiki, Newtown (AU)

(73) Assignee: St. Vincent's Hospital Sydney Limited (AU)

(*) Notice: Subject to any disclaimer, the term of this patent is extended or adjusted under 35 U.S.C. 154(b) by 870 days.

(21) Appl. No.: 12/678,853

(22) PCT Filed: Sep. 22, 2008

(86) PCT No.: PCT/AU2008/001407
§ 371 (c)(1),
(2), (4) Date: Dec. 29, 2010

(87) PCT Pub. No.: WO2009/036521
PCT Pub. Date: Mar. 26, 2009

(65) Prior Publication Data
US 2011/0229448 A1    Sep. 22, 2011

(30) Foreign Application Priority Data

Sep. 20, 2007 (AU) .................................. 2007905154
Sep. 27, 2007 (AU) .................................. 2007905292

(51) Int. Cl.
G01N 33/53    (2006.01)
C12N 5/071    (2010.01)
G01N 33/50    (2006.01)

(52) U.S. Cl.
CPC .................................. G01N 33/505 (2013.01)
USPC ........................................ 435/372.3; 435/7.1

(58) Field of Classification Search
None
See application file for complete search history.

(56) References Cited

U.S. PATENT DOCUMENTS

2003/0147865 A1* 8/2003 Salomon et al. ........... 424/93.21
2004/0224402 A1* 11/2004 Bonyhadi et al. ............. 435/372
2005/0186207 A1* 8/2005 Bluestone et al. ......... 424/144.1

FOREIGN PATENT DOCUMENTS

WO    WO 02/36748 A2         5/2002
WO    WO 2006111986 A1 *   10/2006
WO    WO 2007/014420 A1      2/2007
WO    WO 2007/106939 A1      9/2007

OTHER PUBLICATIONS

Stephens et al., 2004, INt. Immunol. vol. 16: 365-375.*
Zhang et al., 2005, Exp Biol. Meeting abstracts p. A32.*
Nolte-'t Hoen et al., 2004, Eur. J. Immunol. vol. 2004: 3016-3027.*
International Search Report prepared by the Australian Patent Office on Nov. 4, 2008, for International Application No. PCT/AU2008/001407.
Written Opinion prepared by the Australian Patent Office on Oct. 27, 2008, for International Application No. PCT/AU2008/001407.
Seddiki et al. 2006. Expression of interleukin (IL)-2 and IL-7 receptors discriminates between human regulatory and activated T cells. *J Exp Med.* 203:1693-1700.
Deaglio et al. 2007. Adenosine generation catalyzed by CD39 and CD73 expressed on regulatory T cells mediates immune suppression. *J Exp Med.* 204:1257.
Borsellino et al. 2007. Expression of ectonucleotidase CD39 by Foxp3 Treg cells: hydrolysis of extracellular ATP and immune suppression. *Blood*, 110:1225.
Hori et al. 2003. Control of regulatory T cell development by the transcription factor Foxp3. *Science*, 299:1057-1061.
Fontenot et al. 2003. Foxp3 programs the development and function of CD4+CD25+ regulatory T cells. *Nat. Immunol.* 4:330-336.
Khattri et al. 2003. An essential role for Scurfin in CD4+CD25+ T regulatory cells. *Nat. Immunol.* 4:337-342.
Seddiki et al. 2006. Persistence of naïve CD45RA+ regulatory T cells in adult life. *Blood*, 107:2830.
Koenen et al. 2008. Human $CD25^{high}Foxp3^{pos}$ regulatory T cells differentiate into IL-17-producing cells. *Blood* 112:2340.
Fehervari et al. 2006. The dichotomous role of IL-2: tolerance versus immunity. *Trends in Immunol.*, 27:109.
Billerbeck et al. 2007. Parallel expansion of human virus-specific FoxP3—effector memory and de novo-generated FoxP3+ regulatory CD8+ T cells upon antigen recognition in vitro. *J Immunol.* 179:1039-1048.
Vu et al. 2007. OX40 costimulation turns off Foxp3+ Tregs. *Blood* 110:2501.
Curry et al. "OX40 (CD134) blockade inhibits the co-stimulatory cascade and promotes heart allograft survival." Transplantation, Sep. 27, 2004, vol. 78, No. 6, pp. 807-814 (Abstract Only).
Endl et al. "Coexpression of CD25 and OX40 (CD134) Receptors Delineates Autoreactive T-cells in Type 1 Diabetes," Diabetes, Jan. 2006, vol. 55, pp. 50-60.
Huddleston et al. "OX40 (CD134) engagement drives differentiation of CD4+ T cells to effector cells." Eur. J Immunol., May 2006, vol. 36, No. 5, pp. 1093-1103 (Abstract Only).
So et al. "Cutting Edge: OX40 Inhibits TGF-b- and Antigen-Driven Conversion of Naïve CD4 T Cells into CD25+Foxp3+ T cells," The Journal of Immunology, Aug. 2007, vol. 179, No. 3, pp. 1427-1430.
Valzasina et al. "Triggering of OX40 (CD134) on CD4+CD25+ T cells blocks their inhibitory activity: a novel regulatory role for OX40 and its comparison with GITR," Blood, Apr. 2005, vol. 105, No. 7, pp. 2845-2851.
Williams et al. "OX40-Mediated Differentiation to Effector Function Requires IL-2 Receptor Signaling but Not CD28, CD40, IL-12Rβ2, or T-bet," The Journal of Immunology, Jun. 15, 2007, vol. 178, No. 12, pp. 7694-7702.

(Continued)

Primary Examiner — Amy Juedes
(74) Attorney, Agent, or Firm — Sheridan Ross P.C.

(57) ABSTRACT

A method of identifying an antigen-specific regulatory T cell (Treg) from a subject is discussed wherein the method comprises quantitatively or qualitatively detecting co-expression of each of cell markers CD4, CD25 and CD134, or alternatively, each of cell markers CD8, CD25 and CD137, as well as one or more cell markers selected from the group of Treg cell markers consisting of CD39, CD73, CD127, CTLA-4 and Foxp3 on a cell in a suitable lymphocyte-containing sample from the subject in response to exposure to a target antigen. Also discussed are methods of isolating and expanding the identified antigen-specific Treg population, which may permit antigen-specific Treg cell therapy.

18 Claims, 11 Drawing Sheets

(56) References Cited

OTHER PUBLICATIONS

Ahmadzadeh et al., "FOXP3 expression accurately defines the population of intratumoral regulatory T cells that selectively accumulate in metastatic melanoma lesions," Blood, 2008, vol. 112(13), pp. 4953-4960.

Seddiki et al., "Human antigen-specific CD4+CD25+CD134+CD39+ T cells are enriched for regulatory T cells and comprise a substantial proportion of recall responses," Eur. J. Immunol., 2014, vol. 44, pp. 1644-1661.

Zaunders et al., "High Levels of Human Antigen-Specific CD4+ T Cells in Peripheral Blood Revealed by Stimulated Coexpression of CD25 and CD134 (OX40)," J. Immunol., 2009, vol. 183(4), pp. 2827-2836.

* cited by examiner

A

B

TK 44hr P1 stim

METHOD FOR IDENTIFYING ANTIGEN-SPECIFIC REGULATORY T CELLS

CROSS REFERENCE TO RELATED APPLICATIONS

This application is a national stage application under 35 U.S.C. 371 of PCT Application No. PCT/AU2008/001407 having an international filing date of 22 Sep. 2008, which designated the United States, which PCT application claimed the benefit of Australian Application Nos. 2007905154 filed 20 Sep. 2007, and 2007905292 filed 27 Sep. 2007, the entire disclosure of each of which are hereby incorporated herein by reference.

FIELD OF THE INVENTION

The present invention relates to methods for identifying and isolating antigen-specific regulatory T cells.

PRIORITY DOCUMENTS

The present application claims priority from:
Australian Provisional Patent Application No. 2007905154 entitled "A Method" and filed on 20 Sep. 2007; and Australian Provisional Patent Application No. 2007905292 entitled "A Method" and filed on 27 Sep. 2007. The entire content of each of these applications is hereby incorporated by reference.

INCORPORATION BY REFERENCE

The following co-pending patent applications are referred to in the following description:
PCT/AU2006/001080 (WO 2007/014420) titled "METHOD FOR IDENTIFYING REGULATORY T CELLS"; and
PCT/AU2007/000342 (WO 2007/106939) titled "A METHOD FOR DETECTING ANTIGEN SPECIFIC OR MITOGEN ACTIVATED T CELLS".
The entire content of both of these applications is hereby incorporated by reference.

BACKGROUND OF THE INVENTION

T cells are a type of lymphocyte that is involved in immune system regulation and function, particularly those that are driven in response to a specific antigen. Immune cells such as T cells can be identified by the combination of cell markers they express. For example, T cells express cluster of differentiation (CD) 3, which is part of the T cell receptor (TCR) complex. Further, a distinct population of T cells express CD4 (the so-called "helper" T cells), while another distinct population of T cells express CD8 (the so-called "cytotoxic" T cells). The expression marker CD25 is a marker of activation on a number of types of cells, and it is particularly upregulated following stimulation of a cell, notably following antigen stimulation. Activated and memory CD4$^+$ T cells co-express CD4 and CD25.

Regulatory T cells (Treg), also known as "suppressor" T cells, are a specialised subpopulation of T cells that function to suppress activation of the immune system, thereby maintaining immune system homeostasis and tolerance to self-antigens. Treg are accordingly of fundamental importance in suppressing various immune and autoimmune responses. Treg can be identified by their suppressive function as well as by co-expression of T cell markers, for example, CD4, the activation marker CD25 (the α chain of the IL-2 receptor) and the transcription factor Foxp3.

Several different Treg subsets have been described (1). A naturally occurring, distinct population of CD4+CD25+ Foxp3+ Treg known as natural Treg (nTreg) develop in the thymus and are present in healthy individuals from birth. The specificity of the T cell receptor (TCR) of nTreg is mainly self-reactive. Additionally, a population of CD4+CD25+ Foxp3+ Treg can be induced in vivo in the periphery under various conditions, such as during certain defined conditions of antigen presentation and cytokine stimulation, and can induce tolerance (reviewed in (2)). Different subsets of inducible Treg have been reported, including T regulatory type 1 (TR1) cells, which produce high levels of interleukin-1 0 (IL-1 0) (3), a cytokine that has anti-inflammatory actions and facilitates suppression of the antigen presentation capacity of antigen presenting cells. Additionally, a subset of CD4+CD25+Poxp3+ Treg can be induced in vitro from CD4+CD25− T cells in the presence of transforming growth factor-13 (TGF13) (4).

Data generated in several animal models indicates that adoptive transfer of Treg can prevent or cure T cell mediated diseases, autoimmune diseases and allograft rejection, by restoring immune tolerance to self-antigens or alloantigens (5-8). Absent or defective Treg function has been correlated with autoimmunity in humans, and the presence of Treg has been associated with immunological tolerance. Defective Treg in peripheral blood from patients with multiple sclerosis, type-1 diabetes, psoriasis, myasthenia gravis, rheumatoid and juvenile idiopathic arthritis have been described (reviewed in (9)). Defective Treg have also been reported in genetic diseases like immunodysregulation, polyendocrinopathy and enteropathy X-linked syndrome (IPEX)(10), Wiskott-Aldrich syndrome (WAS) (11), autoimmune polyglandular syndrome (APS) type 2 (12) and autoimmune lymphoproliferative syndrome (ALPS) (13).

Accordingly, detecting the presence or absence of Treg cells specific for a particular antigen of interest (ie target antigen) may facilitate diagnosis or assessment of immunological conditions or diseases. Additionally, Treg-based therapy may provide an effective means to treat diseases where suppression of the immune response may be beneficial such as autoimmune diseases, allergic diseases, immunoinflammatory diseases and T cell mediated diseases including genetic diseases. Treg-based therapy may also be useful in suppressing graft rejection, including suppression of graft-versus-host disease (GVHD) after haematopoietic stem cell transplantation (HSCT) (14-16). The use of Treg in the clinic to treat a number of conditions or diseases is currently under consideration by several groups (reviewed in (2)). However, there are a number of issues that are currently impeding Treg therapy.

First, accurate identification of viable Treg using the CD4, CD25 and Foxp3 markers is problematical. Both antigen-experienced conventional effector CD4$^+$ T cells and CD4$^+$ Treg both express CD25. Further, detection of Treg using Foxp3 antibodies requires fixation and permeabilisation of the cells, so the technique cannot be used to isolate viable Treg populations for functional studies or ex vivo expansion as a prelude to therapeutic administration. However, WO 2007/014420 describes a method of detecting viable Treg using the cell marker CD127, the α chain of the interleukin (IL)-7 receptor, in combination with CD4 and CD25. For example, it was shown that CD4$^+$CD25$^+$CD127$^{lo}$ expression is indicative of a regulatory T cell or a population of regulatory T cells (17). More recently, CD39 and CD73, two ectoenzymes that generate adenosine resulting in suppression of T cell responses, have been reported as useful markers for Treg (18-19).

Secondly, Treg are present in low numbers in the circulation. While methods exist to induce and expand Treg ex vivo, Treg have a range of antigen specificities, and in order to suppress a particular inappropriate immune response in certain conditions or diseases (eg autoimmune diseases, allergic diseases, immunoinflammatory diseases, infectious diseases, allograft rejection, and T cell mediated diseases including genetic diseases), Treg need to specifically recognise the antigen involved in the response. However, methods of detecting the antigen specificity of Treg have not previously been described.

WO 2007/106939 describes a highly sensitive flow cytometric assay which is capable of identifying antigen specific effector (conventional) CD4+ or CDS+ T cells using antibodies directed to the cell marker CD25, in combination with antibodies directed to one or more of CD134 (also known as OX40) and, CD137 (also known as 4-1BB) following exposure to the target antigen. For example, following in vitro exposure to a particular target antigen in whole blood, CD4+ T cells that were specific for that antigen were shown to co-express CD25 and CD134. However, Treg were not thought to be identified by this method. CD134 is not expressed in CD4+CD25+ Treg cells isolated from human blood (32). Further, a recent report indicates that stimulation of CD134 on Treg by an anti-CD134 antibody down regulated Foxp3 expression and reduced Treg function in mice (48).

The present applicant has found that antigen-specific CD4$^+$ Treg can be identified by detecting cells expressing the combination of CD4, CD25, CD134 and one or more Treg markers, such as CD39, CD127 (wherein CD127 expression is preferably CD127$^{lo}$) and Foxp3; and further, that antigen-specific CD8$^+$ Treg can be identified by the expression of the combination of CD8, CD25, CD137 and one or more Treg cell markers, such as CD39, CD127 (wherein CD127 expression is preferably) CD127$^{lo}$) and Foxp3. Surprisingly, the present applicant has also found that viable antigen-specific Treg can be identified and/or isolated using combinations of the cell markers CD4, CD8, CD25, CD39, CD45RO, CD45RA, CD127, CD134 and CD137. Moreover, it was found that using such combinations of these cell markers provides a means to isolate Treg of high purity, which may be ex vivo expanded, for use in, for example, Treg-based therapy.

SUMMARY OF THE INVENTION

In a first aspect, the present invention provides a method of identifying an antigen-specific regulatory T cell (Treg) from a subject, the method comprising quantitatively or qualitatively detecting co-expression of each of cell markers CD4, CD25 and CD134 as well as one or more cell markers selected from the group of Treg cell markers consisting of CD39, CD73, CD127, CTLA-4 and Foxp3 on a cell in a suitable lymphocyte-containing sample from the subject in response to exposure to a target antigen, wherein detecting the co-expression of the cell markers is indicative of an antigen-specific Treg.

In a second aspect, the present invention provides a method of identifying an antigen-specific regulatory T cell (Treg) from a subject, the method comprising quantitatively or qualitatively detecting co-expression of each of cell markers CD8, CD25 and CD137 as well as one or more cell markers selected from the group of Treg cell markers consisting of CD39, CD73, CD127, CTLA-4 and Foxp3 on a cell in a suitable lymphocyte-containing sample from the subject in response to exposure to a target antigen, wherein detecting the co-expression of the cell markers is indicative of an antigen-specific Treg.

In a third aspect, the present invention provides a method of isolating antigen-specific Treg from a subject comprising isolating the cells identified according to the method of the first and second aspects of the invention.

In a fourth aspect, the present invention provides a method of isolating an antigen-specific regulatory T cell (Treg) from a subject, the method comprising the following steps:
 (i) providing isolated naïve Treg or activated Treg expressing one or more cell markers selected from the group of consisting of CD39, CD45RA, CD45RO, CD73, CD127 and CTLA-4 from a suitable lymphocyte-containing sample from the subject,
 (ii) culturing said isolated naïve or activated Treg in the presence of a target antigen in vitro, and thereafter
 (iii) isolating antigen-specific Treg co-expressing each of the cell markers CD4, CD25 and CD134.

In a fifth aspect, the present invention provides a method of isolating antigen-specific Treg from a subject, the method comprising the following steps:
 (i) providing isolated naïve Treg or activated Treg expressing one or more cell markers selected from the group consisting of CD39, CD62L, CD45RO, CD73, CD127 and CTLA-4 from a suitable lymphocyte-containing sample from the subject; and
 (ii) culturing said isolated naïve or activated Treg in the presence of an antigen; and thereafter
 (iii) isolating antigen-specific Treg cells expressing each of the cell markers CD8, CD25 and CD137.

In a sixth aspect, the present invention provides a method of providing an expanded population of antigen-specific Treg the method comprising expanding in vitro the population of antigen-specific Treg isolated in accordance with the method of the third, fourth or fifth aspects of the invention.

In a seventh aspect, the present invention provides a method of cell therapy comprising administering antigen-specific Treg isolated according to the method of the third, fourth or fifth aspects of the invention to a subject.

In an eighth aspect, the present invention provides a method of cell therapy comprising administering the antigen-specific Treg population expanded according to the sixth aspect of the invention to a subject.

DETAILED DESCRIPTION OF THE INVENTION

Figure 1:
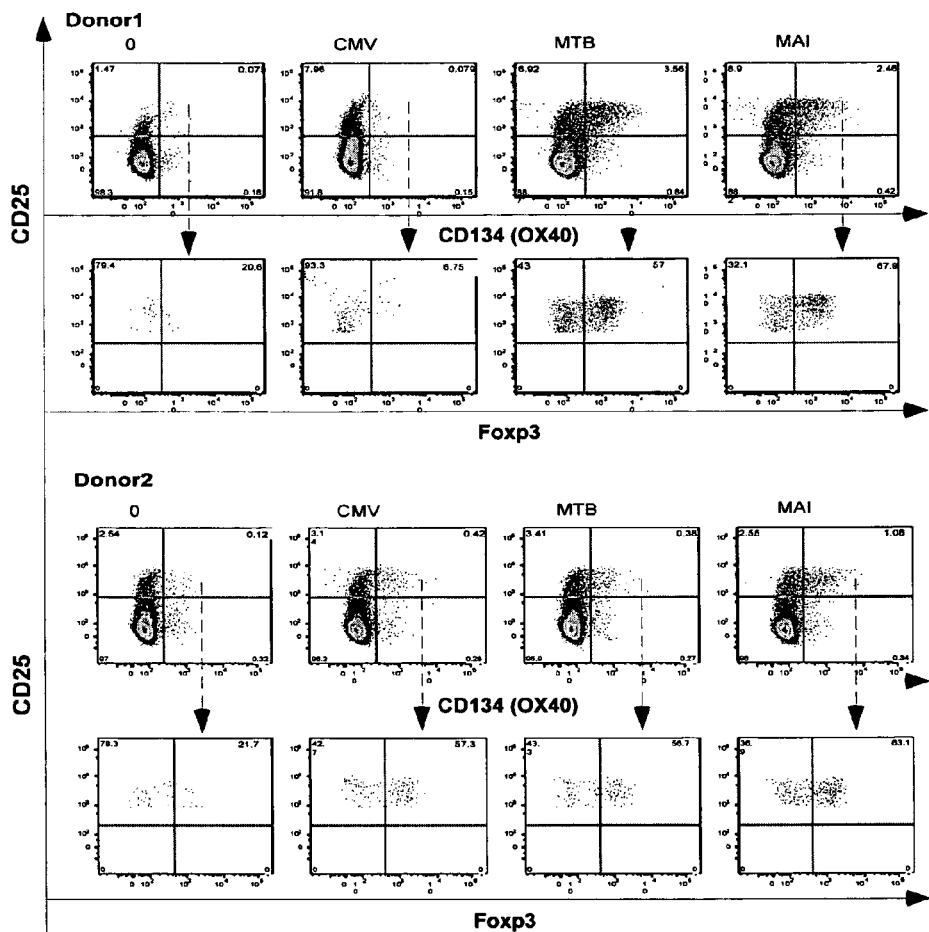
FIG. 1 provides FACS analysis plots of CD4$^+$CD25$^+$CD134$^+$Foxp3$^+$ antigen-specific Treg following antigen stimulation in vitro for 24-40 hours. Cells were stained with anti-CD3, anti-CD4, anti-CD25, anti-CD134 and anti-Foxp3 monoclonal antibodies. Antigen-specific Treg were gated as CD3$^+$CD4$^+$CD25$^+$CD134$^+$Foxp3$^+$. For each donor, the bottom panel shows Foxp3 expression on the CD25$^+$CD134$^+$ subset shown in the top panel. (A) Whole blood from donor 1 and 2 was in vitro stimulated with no antigen, CMV, MTB or MAI lysates. (B) Whole blood from donor 1 was in vitro stimulated with no antigen, CMV-P1 peptide antigen, or SEB (as a positive control)
Figure 1:
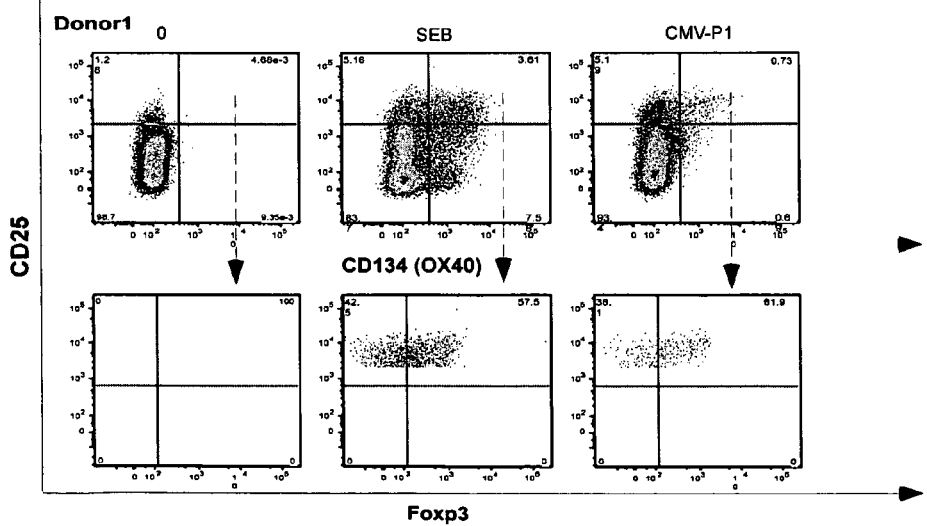

The present applicant has provided a method for identifying and isolating antigen-specific regulatory T cells (Treg).

The term "antigen-specific" as used herein to describe a cell (eg a CD4$^+$CD25$^+$CD134$^+$ or a CD8$^+$CD25$^+$CD137$^+$ T cell, including Treg) is to be understood as referring to a cell that is able to specifically recognise and respond to a target antigen, wherein a "target antigen" is a particular antigen of interest. Persons skilled in the art will understand that each T cell in a population can specifically recognise and respond to an antigen through its T cell receptor (TCR); however, a population of T cells will contain only a small percentage of cells that can specifically recognise and respond to the target antigen.

The term "non-antigen-specific", as used herein to describe cells (eg CD4$^+$CD25$^+$CD134$^-$ or CD8$^+$CD25$^+$CD137$^-$ T cells) is to be understood as referring to cells that do not specifically bind or respond to the target antigen.

The term "regulatory T cell" will be well understood by persons skilled in the art and refers to a specialised subpopulation of T cells that function to suppress activation of the immune system. The term "Treg" refers to regulatory T cells, in either the singular or the plural.

It has previously been established that following culturing with a target antigen, antigen-specific effector (conventional) T cells can be identified by detecting the co-expression of CD4, CD25 and CD134, or alternatively, CD8, CD25 and CD137 (see WO 2007/106939, the entire contents of which are hereby incorporated herein). However, this method was not thought to detect Treg. The present applicant surprisingly found that following in vitro stimulation of a lymphocyte-containing population with a target antigen, a population of CD4$^+$CD25$^+$CD134$^+$ antigen-specific T cells express the Treg marker Foxp3. The present applicant also found that antigen-specific Treg could be identified by detecting expression of CD4, CD25, CD134 and one or more alternative Treg markers, for example, CD39, CD73, CD127, or Foxp3.

Accordingly, in a first aspect, the present invention provides a method of identifying an antigen-specific regulatory T cell (Treg) from a subject, the method comprising quantitatively or qualitatively detecting co-expression of each of cell markers CD4, CD25 and CD134 as well as one or more cell markers selected from the group of Treg cell markers consisting of CD39, CD73, CD127, CTLA-4 and Foxp3 on a cell in a suitable lymphocyte-containing sample from the subject in response to exposure to a target antigen, wherein detecting the co-expression of the cell markers is indicative of an antigen-specific Treg.

The term "co-expression" as used herein will be understood by persons skilled in the art to refer to the presence of more than one cell marker of interest on the same cell. For example, a CD4$^+$CD25$^+$ cell is understood to co-express the cell markers CD4 and CD25. The term "on a cell" as used herein in relation to the expression of cell markers, is intended to mean that the cell marker is present on the cell (in the case of cell surface markers) or within the cell (in the case of intracellular cell markers).

In an embodiment of the first aspect, the method may comprise the following steps:
(i) culturing the suitable lymphocyte-containing sample from the subject in vitro in the presence of the target antigen; and thereafter
(ii) quantitatively or qualitatively detecting co-expression of each of the cell markers CD4, CD25 and CD134 as well as one or more cell markers selected from the group of Treg cell markers consisting of CD39, CD73, CD127, CTLA-4 and Foxp3 in the cultured sample.

The term "culturing" as used herein in the context of culturing cells in the presence of a target antigen will be understood by persons skilled in the art to facilitate antigen stimulation of cells that are able to specifically recognise and respond to the target antigen.

It will be understood that in some preferred embodiments the cell markers detected may be CD4, CD25, CD134 and Foxp3; in other preferred embodiments, the cell markers detected are CD4, CD25, CD134 and CD39; and in still other embodiments, the cell markers detected are CD4, CD25, CD134 and CD127; and in yet still other preferred embodiments, the cell markers detected are CD4, CD25, CD134, CD39 and CD127.

Preferably, where CD127 is detected, the method comprises detecting a CD127$^{lo}$ level of detection.

The term "$^{lo}$", as used in relation to CD127$^{lo}$ for example, is well known to persons skilled in the art to refer to the expression level of the cell marker of interest, in that the expression level of the cell marker is low by comparison with the expression level of that cell marker in the population of cells being analysed as a whole. More particularly, the term "$^{lo}$" refers to a distinct population of cells that express the cell marker at a lower level than one or more other distinct populations.

Preferably, the phenotype of an antigen-specific CD4$^+$ Treg is CD3$^+$CD4$^+$CD25$^+$CD39$^+$CD127$^{lo}$CD134$^+$Foxp3$^+$. However, persons skilled in the art will understand that it is not necessary to detect each of the Treg cell markers (eg CD39, CD127 and Foxp3) to determine that it is a CD4$^+$ antigen-specific Treg. That is, it will be understood that in some preferred embodiments, alternative Treg cell markers can be used to detect antigen-specific Treg. For example, the method for the detection of antigen-specific regulatory T cells in a subject may comprise detecting expression of both of the cell markers CD4 and CD25; as well as detecting expression of a cell marker of CD4+ antigen-specific T cells (eg CD134); as well as detecting expression of one or more the cell markers for Treg (eg CD39, CD73, CD127$^{lo}$, CTLA-4, Foxp3, CD45RO, CD45RA, LAG-3, and GPR83). Further, CD3 forms part of the TCR and is accordingly considered to be a pan marker for T cells. Persons skilled in the art will understand that it is not essential to detect CD3 in order to identify antigen-specific Treg.

Preferably, the step of detecting co-expression of each of the cell markers CD4, CD25 and CD134 as well as one or more cell markers selected from the group of Treg cell markers consisting of CD39, CD73, CD127, CTLA-4 and Foxp3 in the cultured sample is performed before a substantial number of the cells present in the culture have divided. Accordingly, under standard culturing conditions (eg 37° C. in a humidified atmosphere of 5% CO$_2$ in air, and using a standard culture medium suitable for the culture of lymphocytes), the detecting step is preferably performed within about 24 to 96 hours of commencement of the culturing step, and more preferably, within about 40 to 44 hours of commencement of the culturing of the whole blood sample in the presence of the antigen. Moreover, it is preferable that the detecting step is performed after the elapse of a sufficient period for co-expression of the cell markers to be substantially up-regulated. In some preferred embodiments, the detecting step is performed within about 40 to 44 hours of commencement of the culturing step.

The step of detecting the cell surface markers may be performed in accordance with any method well known to persons skilled in the art. Such a method may involve the use of labelled monoclonal antibodies that specifically bind to one of the cell surface markers selected from the group consisting of CD4, CD25, CD134, CD39, CD73, CD127, CTLA-4 and Foxp3. The detecting step may utilise methods well known to persons skilled in the art, for example, using antibody-coated magnetic beads, enzyme-linked immunoassay or real-time polymerase chain reaction. Preferably, the detecting step comprises the use of flow cytometry. In this regard, persons skilled in the art will understand that following binding with suitable, labelled monoclonal antibodies (eg anti-CD4, anti-CD25, anti-CD134 and anti-CD127 antibodies), samples may be fixed with a suitable fixing agent (eg paraformaldehyde, which may be used at 1% in phosphate-buffered saline (PBS)) to permit the subsequent quantitative or qualitative determination of the cell surface markers (eg by the use of flow cytometry) as convenient (eg following transport from the site of collection and culture of the whole blood sample, to a flow cytometry laboratory). In some cases, the timing of the detecting step may be delayed for a few hours or a few days, if, for example, the cultured cells are fixed, and/or stored at a low temperature (eg on ice or in a refrigerator), including storage in the dark. Accordingly, in the context of the preferred times, given above, for performing the detecting step, it is to be understood that the "staining" (ie with suitable monoclonal antibodies labelled with a fluorescent dye(s)) and "fixing" of the cultured samples need only be performed within the given preferred time period. That is, it is to be understood that where the staining and fixing is initiated 44 hours after commencement of the culturing of the whole blood sample in the presence of the antigen, but the actual quantitative or qualitative determination of the cell surface markers is not performed until later (eg 12 to 24 hours later, or a few days later), that nevertheless amounts to performing the detecting step within the most preferred time period of about 24 to 96 hours of commencement of the culturing of the whole blood sample in the presence of the antigen. Persons skilled in the art will understand that monoclonal antibodies used to detect expression of cell markers CD4, CD8, CD25, CD39, CD45RO, CD45RA, CD62L, CD127, CD134, or CD137 in accordance with the invention have been used only to stain cells for flow cytometry, and have not been used to stimulate or block signalling of the cell marker.

In some embodiments, the lymphocyte-containing sample may be a whole blood sample or more preferably, the whole blood sample is a heparinised whole blood sample. Alternatively, the lymphocyte-containing sample may be a purified peripheral blood mononuclear cell sample.

The whole blood sample can be obtained from the subject by any method well known to persons skilled in the art (eg by cannula and the use of blood sample vials). A suitable anticoagulant agent may be added to the whole blood sample to prevent clotting. A particularly suitable anticoagulant agent is sodium heparin which can be conveniently used by employing any commercially available heparinised blood sample vials. Preferably, anticoagulant agents which chelate calcium ions (Ca$^{2+}$), such as acid-citrate dextrose (ACD) or ethylene diaminetetracetic acid (EDTA), are avoided as these may interfere with lymphocyte function by preventing calcium influx. Accordingly, it is preferable that whole blood samples, for use in the method of the first aspect, are collected in heparinised blood sample vials.

The peripheral blood mononuclear cell (PBMC) sample can be prepared from whole blood using purification techniques well known to those skilled in the art, for example, purification using a Ficoll-Paque gradient, or extraction from whole blood by hypotonic lysis that preferentially lyses red blood cells.

The step of culturing the whole blood sample or the PBMC sample may be in accordance with any method well known to persons skilled in the art. The whole blood sample or the PBMC sample may be, for example, mixed with a suitable culture medium (eg Iscove's modified Dulbecco's medium) and antigen, and incubated at 37° C.

The target antigen will be selected in accordance with the intended antigen-specific Treg to be detected. In some preferred embodiments, the target antigen is selected from the group consisting of tuberculin, Hepatitis C Virus (HCV) core antigen, HCV nonstructural protein 3 (NS3), cytomegalovirus (CMV) phosphoprotein 65 (pp65), CMV lysate, CMV peptides, Herpes Simplex Virus (HSV)-1 lysate, HSV-2 lysate, vaccinia lysate, tetanus toxoid (TT), purified protein derivative (PPD) from *Mycobacterium tuberculosis, Streptococcus* antigen streptokinase, Human Immunodeficiency virus (HIV)-1 p24, pools of overlapping peptides from HIV-1 Gag, Env, Pol or other accessory proteins, SSA/SSB ribonucleoprotein particle.

It is to be understood that Treg specific for foreign antigens may function to down-regulate the immune response raised in response to the said antigens. This may be beneficial to a subject where an over-active immune response to the antigen is associated with host-mediated tissue damage and disease progression.

In some preferred embodiments, the target antigen is selected from self-antigens involved with autoimmune diseases. It is well known that determining the exact antigens in human cases of autoimmune disease is difficult to determine (20). It is, however, to be understood that antigens may be selected from a group of self-antigens that are implicated in various autoimmune disorders. For example, in multiple sclerosis, the antigen may be derived from myelin; in type 1 diabetes, the antigen may be derived from insulin, proinsulin and from the beta cells of the islets of Langerhans of the pancreas; and in myasthenia gravis, the antigen may be derived from the acetylcholine receptor. However, it is to be understood that other self-antigens involved in these diseases are also of interest. Preferably, the antigen is selected from the group of self-antigens involved in multiple sclerosis, type 1 diabetes, psoriasis, myasthenia gravis, rheumatoid arthritis, juvenile idiopathic arthritis, IPEX, WAS, APS, ALPS, as well as self-antigens that may be involved in graft-versus-host disease following an allograft transplant. It is to be understood that Treg specific for these self-antigens may function to down-regulate an inappropriate autoimmune response raised in response to the said antigens.

In some preferred embodiments, the target antigen is selected from the group of allo-antigens present in an allograft. In this context, it is to be understood that Treg specific for these allo-antigens may function to down-regulate an inappropriate immune response raised in response to the said antigens, for example, during a host-mediated rejection of an allograft transplant.

In some preferred embodiments, the target antigen is derived from allergens. It is to be understood that Treg specific for these allergens may function to down-regulate an inappropriate allergic immune response raised in response to the said allergens.

Additionally, in some diseases, such as type 1 diabetes associated with IPEX, psoriasis, myasthenia gravis, autoimmune polyglandular syndrome type II and WAS, Treg may have functional deficiencies (10-13). Accordingly, treatment with any antigen-specific or mitogen-activated Treg that has been ex vivo activated and expanded may be beneficial to the subject. Alternatively, in some diseases such as some cancers, it may be beneficial to identify and deplete Treg specific for a particular target antigen such as a tumour antigen, as they may suppress anti-tumour T cell immune response that facilitate immunological rejection of tumours (21).

Accordingly, in some embodiments, the target antigen is a mitogen or a polyclonal activator of the TCR. For example, the sample may be in vitro cultured with mitogen. The mitogen may be selected from those mitogens well known to persons skilled in the art, for example, the mitogen may be selected from the group consisting of PHA, phorbol myristyl acetate (PMA), ionomycin, *Staphylococcal* enteroantigen B (SEB), toxic shock syndrome toxin (TSST), *Staphylococcal enterotoxin* A (SEA), concanavalin A (Con A) and pokeweed mitogen. Alternatively, the sample may be in vitro cultured an agent that stimulates the TCR polyclonally, that is, without antigen specificity. For example, the sample may be in vitro cultured with monoclonal antibodies that are known to polyclonally stimulate the TCR, for example, anti-CD3, anti-CD2, anti-CD28 or anti-CD49d, or combinations thereof. For example, polyclonal TCR stimulation may utilise an anti-CD3 monoclonal antibody optionally in combination with an anti-CD28 monoclonal antibody and/or an anti-CD2 monoclonal antibody.

In some embodiments of the first aspect of the present invention, the subject is human.

In a second aspect, the present invention provides a method of identifying an antigen-specific regulatory T cell (Treg) from a subject, the method comprising quantitatively or qualitatively detecting co-expression of each of cell markers CD8, CD25 and CD137 as well as one or more cell markers selected from the group of Treg cell markers consisting of CD39, CD73, CD127, CTLA-4 and Foxp3 on a cell in a suitable lymphocyte-containing sample from the subject in response to exposure to a target antigen, wherein detecting the co-expression of the cell markers is indicative of an antigen-specific Treg.

In an embodiment of the second aspect, the method comprises the following steps:
 (i) culturing the suitable lymphocyte-containing sample from the subject in vitro in the presence of the target antigen; and thereafter
 (ii) quantitatively or qualitatively detecting expression of each of the cell markers CD8, CD25 and CD137 as well as one or more of cell markers selected from the group of Treg markers consisting of CD39, CD73, CD127, CTLA-4 and Foxp3 in the cultured sample.

It will be understood that in some preferred embodiments the cell markers detected may be CD8, CD25, CD137 and Foxp3; in other preferred embodiments, the cell markers detected are CD8, CD25, CD137 and CD39; and in still other embodiments, the cell markers detected are CD8, CD25, CD137 and CD127; and in yet still other preferred embodiments, the cell markers detected are CD8, CD25, CD137, CD39 and CD127.

Preferably, where CD127 is detected, the method comprises a CD127$^{lo}$ level of expression.

Preferably, the phenotype of an antigen-specific CD8$^+$ Treg is CD3$^+$CD8$^+$CD25$^+$CD39$^+$CD127$^{lo}$CD137$^+$Foxp3$^+$, although persons skilled in the art will understand that it is not necessary to detect each of the Treg cell markers (eg CD39, CD127 and Foxp3) to determine that it is a CD8$^+$ antigen-specific Treg. That is, it will be understood that in some preferred embodiments, alternative markers can be used to detect antigen-specific Treg. For example, the method for the detection of antigen-specific regulatory T cells in a subject may comprise detecting expression of each of the cell markers CD8 and CD25; as well as detecting expression of a cell marker of CD8+ antigen-specific T cells (eg CD137); as well as detecting expression levels of one or more of the cell markers for Treg (eg CD39, CD73, CD127$^{lo}$, CTLA-4, Foxp3, CD45RO, CD45RA, LAG-3, and GPR83).

Preferably, the step of detecting co-expression of each of the cell markers CD8, CD25 and CD137 as well as one or more cell markers selected from the group of Treg cell markers consisting of CD39, CD73, CD127, CTLA-4 and Foxp3 in the cultured sample is performed before a substantial number of the cells present in the culture have divided. Accordingly, under standard culturing conditions (eg 37° C. in a humidified atmosphere of 5% $CO_2$ in air, and using a standard culture medium suitable for the culture of lymphocytes), the detecting step is preferably performed within about 24 to 96 hours of commencement of the culturing step, and more preferably, within about 40 to 44 hours of commencement of the culturing of the whole blood sample in the presence of the antigen. Moreover, it is preferable that the detecting step is performed after the elapse of a sufficient period for co-expression of the cell markers to be substantially up-regulated. In some preferred embodiments, the detecting step is performed within about 40 to 44 hours of commencement of the culturing step.

The step of detecting the cell surface markers may be performed in accordance with any method well known to persons skilled in the art. Such a method may involve the use of labelled monoclonal antibodies that specifically bind to one of the cell surface markers selected from the group consisting of CD8, CD25, CD137, CD39, CD73, CD127, CTLA-4 and Foxp3. The detecting step may utilise methods known to persons skilled in the art, for example, using antibody-coated magnetic beads, enzyme-linked immunoassay or real-time polymerase chain reaction. Preferably, the detecting step comprises the use of flow cytometry. In this regard, persons skilled in the art will understand that following binding with suitable, labelled monoclonal antibodies (eg anti-CD8, anti-CD25, anti-CD137 and anti-CD127 antibodies), samples may be fixed with a suitable fixing agent (eg paraformaldehyde, which may be used at 1% in phosphate-buffered saline (PBS)) to permit the subsequent quantitative or qualitative determination of the cell surface markers (eg by the use of flow cytometry) as convenient (eg following transport from the site of collection and culture of the whole blood sample, to a flow cytometry laboratory). In some cases, the timing of the detecting step may be delayed for a few hours or a few days, if, for example, the cultured cells are fixed, and/or stored at a low temperature (eg on ice or in a refrigerator), including storage in the dark. Accordingly, in the context of the preferred times, given above, for performing the detecting step, it is to be understood that the "staining" (ie with suitable monoclonal antibodies labelled with a fluorescent dye(s)) and "fixing" of the cultured samples need only be performed within the given preferred time period. That is, it is to be understood that where the staining and fixing is initiated 44 hours after commencement of the culturing of the whole blood sample in the presence of the antigen, but the actual quantitative or qualitative determination of the cell surface markers is not performed until later (eg 12 to 24 hours later, or a few days later), that nevertheless amounts to performing the detecting step within the most preferred time period of about 24 to 96 hours of commencement of the culturing of the whole blood sample in the presence of the antigen. Persons skilled in the art will understand that monoclonal antibodies used to detect expression of cell markers CD4, CD8, CD25, CD39, CD45RO, CD45RA, CD62L, CD127, CD134, or CD137 in accordance with the invention have been used only to stain cells for flow cytometry, and have not been used to stimulate or block signalling of the cell marker.

In some embodiments of the second aspect, the lymphocyte-containing sample may be a whole blood sample or more preferably, the whole blood sample is a heparinised whole blood sample. Alternatively, the lymphocyte-containing sample may be a purified peripheral blood mononuclear cell sample.

The whole blood sample can be obtained from the subject by any method well known to persons skilled in the art (eg by cannula and the use of blood sample vials). A suitable anticoagulant agent may be added to the whole blood sample to prevent clotting. A particularly suitable anticoagulant agent is sodium heparin which can be conveniently used by employing any commercially available heparinised blood sample vials. Preferably, anticoagulant agents which chelate calcium ions ($Ca^{2+}$), such as acid-citrate dextrose (ACD) or ethylene diaminetetracetic acid (EDTA), are avoided as these may interfere with lymphocyte function by preventing calcium influx. Accordingly, it is preferable that whole blood samples, for use in the method of the second aspect, are collected in heparinised blood sample vials.

The peripheral blood mononuclear cell (PBMC) sample can be prepared from whole blood using purification techniques well known to those skilled in the art, for example, purification using a Ficoll-Paque gradient, or extraction from whole blood by hypotonic lysis that preferentially lyses red blood cells.

The step of culturing the whole blood sample or the PBMC sample may be in accordance with any method well known to persons skilled in the art. The whole blood sample or the PBMC sample may be, for example, mixed with a suitable culture medium (eg Iscove's modified Dulbecco's medium) and antigen, and incubated at 37° C.

The target antigen will be selected in accordance with the intended antigen-specific Treg to be detected. In some preferred embodiments, the target antigen is selected from the group consisting of tuberculin, Hepatitis C Virus (HCV) core antigen, HCV nonstructural protein 3 (NS3), cytomegalovirus (CMV) phosphoprotein 65 (pp65), CMV lysate, CMV peptides, Herpes Simplex Virus (HSV)-1 lysate, HSV-2 lysate, vaccinia lysate, tetanus toxoid (TT), purified protein derivative (PPD) from *Mycobacterium tuberculosis, Streptococcus* antigen streptokinase, Human Immunodeficiency virus (HIV)-1 p24, pools of overlapping peptides from HIV-1 Gag, Env, Pol or other accessory proteins, SSA/SSB ribonucleoprotein particle.

In some preferred embodiments of the second aspect, the target antigen is selected from self-antigens involved with autoimmune diseases as described above in relation to the first aspect.

In some preferred embodiments of the second aspect, the target antigen is selected from the group of allo-antigens present in an allograft.

In some preferred embodiments of the second aspect, the target antigen is derived from allergens.

In some embodiments of the second aspect, the subject may be human.

In a third aspect, the present invention provides a method of isolating antigen-specific Treg from a subject comprising isolating the cells identified according to the method of the first and second aspects of the invention.

Preferably, the isolation of the antigen-specific Treg comprises the use of at least one monoclonal antibody selected from the group of monoclonal antibodies, which specifically bind to one of CD4, CD8, CD25, CD39, CD73, CD127, CD134, CD137, CTLA-4 and Foxp3. Further, the isolation preferably comprises the use of flow cytometry, particularly the cell sorting aspects of flow cytometry. However, persons skilled in the art will understand that the antigen-specific Treg may be isolated using other methods, for example, by using antibody-coated magnetic beads.

In a fourth aspect, the present invention provides a method of isolating a $CD4^+$ antigen-specific regulatory T cell (Treg) from a population of isolated naïve or activated Treg following culturing with the target antigen.

The term "naïve" is well known to persons skilled in the art and is understood to refer to an immune cell, or a population of immune cells, that have not yet encountered any specific antigen. Naïve T cells can be distinguished from activated or memory cells by the isoform of the cell marker CD45 expressed. For example, naïve T cells are considered to be $CD45RA^+$ and $CD45RO^-$. In contrast, activated and memory T cells are considered to be $CD45RA^-$ and $CD45RO^+$.

Accordingly, in an embodiment of the fourth aspect, the present invention provides a method of isolating an antigen-specific regulatory T cell (Treg) from a subject, the method comprising the following steps:
(i) providing isolated naïve Treg or activated Treg expressing one or more cell markers selected from the group consisting of CD39, CD45RA, CD45RO, CD73, CD127 and CTLA-4 from a suitable lymphocyte-containing sample from the subject,
(ii) culturing said isolated naïve or activated Treg in the presence of a target antigen in vitro, and thereafter
(iii) isolating antigen-specific Treg co-expressing each of the cell markers CD4, CD25 and CD134.

In a preferred embodiment, the fourth aspect provides a method of isolating antigen-specific Treg following culturing of isolated naïve Treg with the target antigen. Preferably, the method comprises the following steps:
(i) isolating $CD4^+CD25^+CD45RO^-CD127^{lo}$ naïve Treg or $CD4^+CD25^+CD45RA^+CD127^{lo}$ naïve Treg from a suitable lymphocyte-containing sample from the subject;
(ii) culturing said isolated cells in the presence of a target antigen in vitro; and thereafter
(iii) isolating $CD4^+CD25^+CD134^+$ antigen-specific Treg cells from the cultured sample.

In an embodiment, step (i) may comprise isolating $CD4^+CD25^+CD45RO^-CD62L^+CD127^{lo}$ naïve Treg or $CD4^+CD25^+CD45RA^+CD62L^+CD127^{lo}$ naïve Treg from a suitable lymphocyte-containing sample from the subject.

Preferably, the step of isolating antigen-specific $CD4^+CD25^+CD134^+$ Treg in the cultured sample occurs before a substantial number of cells present in the culture have divided in response to the antigen. Preferably, the antigen-specific Treg isolating step of the method is performed within about 24 to 96 hours of commencement of the culturing step. More preferably, the antigen-specific Treg isolating step is performed within about 40 to 44 hours of commencement of the culturing step. However, naïve Treg may require a longer time period to respond to antigen than activated Treg. Accordingly, in some preferred embodiments, the antigen-specific Treg isolating step is performed within about 72 hours of commencement of the culturing step.

The fourth aspect also provides a method of isolating antigen-specific Treg following culturing of isolated activated Treg with the target antigen. Preferably, the method comprises the following steps:
(i) isolating $CD4^+CD25^+CD45RO^+$ activated Treg or $CD4^+CD25^+CD45RA^-$ activated Treg from a suitable lymphocyte-containing sample from the subject;
(ii) culturing said isolated cells in the presence of the target antigen; and thereafter
(iii) isolating $CD4^+CD25^+CD134^+$ antigen-specific Treg cells from the cultured sample.

In an embodiment, step (i) may comprise isolating $CD4^+CD25^+CD45RO^+CD62L^{+/-}$ activated Treg or $CD4^+CD25^+CD45RA^-CD62L^{+/-}$ activated Treg from a suitable lymphocyte-containing sample from the subject. In another embodiment, step (i) may comprise isolating $CD4^+CD25^+CD45RO^+CD62L^{+/-}CD127^{lo}$ activated Treg or $CD4^+CD25^+CD45RA^-CD62L^{+/-}CD127^{lo}$ activated Treg from a suitable lymphocyte-containing sample from the subject. More preferably, step (i) comprises isolating $CD4^+CD25^+CD45RO^+CD127^{lo}$ activated Treg or $CD4^+CD25^+CD45RA^-CD127^{lo}$ activated Treg.

Preferably, the step of isolating antigen-specific $CD4^+CD25^+CD134^+$ Treg in the cultured sample occurs before a substantial number of cells present in the culture have divided in response to the antigen. Accordingly, it is preferred if the antigen-specific Treg isolating step of the method is performed within about 24 to 96 hours of commencement of the culturing step. More preferably, the antigen-specific Treg isolating step is performed within about 40 to 44 hours of commencement of the culturing step. In some embodiments, the antigen-specific Treg isolating step is performed within about 72 hours of commencement of the culturing step.

Preferably, step (iii) of the method of the fourth aspect comprises isolating $CD4^+CD25^+CD134^+$ cells that also co-express one or more cell markers selected from the group of Treg cell markers consisting of CD39, CD45RO, CD73, CD127, CTLA-4 and Foxp3. Preferably, step (iii) comprises isolating $CD4^+CD25^+CD134^+$ cells that also co-express the Treg cell markers CD39 and CD127.

Preferably, where CD127 is detected, the method comprises a $CD127^{lo}$ level of expression.

It will be understood that in some preferred embodiments, alternative markers can be used to isolate antigen-specific Treg. For example, the method for the isolation of $CD4^+$ antigen-specific regulatory T cells in a subject may comprise isolating $CD4^+$ Treg in step (i) using CD4 and one or more Treg cell markers in the art (eg CD39, CD73, $CD127^{lo}$, CTLA-4, CD45RO, CD45RA, LAG-3, and GPR83) and then isolating $CD4^+$ antigen-specific Treg in step (iii) using one or more of the $CD4^+$ antigen-specific T cell markers (eg CD134).

In some embodiments, the antigen is selected from the group consisting of tuberculin, Hepatitis C Virus (HCV) core antigen, HCV nonstructural protein 3 (NS3), cytomegalovirus (CMV) phosphoprotein 65 (pp65), CMV lysate, CMV peptides, Herpes Simplex Virus (HSV)-1 lysate, HSV-2 lysate, vaccinia lysate, tetanus toxoid (TT), purified protein derivative (PPD) from *Mycobacterium tuberculosis, Streptococcus* antigen streptokinase, Human Immunodeficiency virus (HIV)-1 p24, pools of overlapping peptides from HIV-1 Gag, Env, Pol or other accessory proteins, SSA/SSB ribonucleoprotein particle.

In some preferred embodiments of the fourth aspect, the antigen is selected from self-antigens involved with autoimmune diseases.

In some preferred embodiments of the fourth aspect, the antigen is selected from the group of allo-antigens present in an allograft.

In other preferred embodiments of the fourth aspect, the antigen is derived from allergens.

In some embodiments of the method of the fourth aspect, the lymphocyte-containing sample may be a whole blood sample, or more preferably, the whole blood sample is a heparinised whole blood sample. Alternatively, the lymphocyte-containing sample may be a purified peripheral blood mononuclear cell sample. Preferably, the subject may be human.

In some embodiments, at least one of the isolating steps comprise the use of at least one monoclonal antibody selected from the group of monoclonal antibodies which specifically bind to one of CD4, CD25, CD39, CD45RA, CD45RO, CD73, CD127, CD134 and CTLA-4. In some embodiments, the isolating step comprises the use of flow cytometry.

In a fifth aspect, the present invention provides a method of isolating an CD8+ antigen-specific regulatory T cell (Treg) from a population of isolated naïve or activated Treg following culturing with a target antigen.

Accordingly, in an embodiment of the fifth aspect, the present invention provides a method of isolating antigen-specific Treg from a subject, the method comprising the following steps:
(i) providing isolated naïve Treg or activated Treg expressing one or more cell markers selected from the group of cell markers consisting of CD39, CD45RO, CD73, CD127 and CTLA-4 from a suitable lymphocyte-containing sample from the subject; and
(ii) culturing said isolated naïve or activated Treg in the presence of a target antigen; and thereafter
(iii) isolating antigen-specific Treg cells expressing each of the cell markers CD8, CD25 and CD137.

In an embodiment, step (i) may comprise isolating CD8+CD25+CD45RO−CD127$^{lo}$ naïve Treg or CD8+CD25+CD45RA+CD127$^{lo}$ naive Treg from a suitable lymphocyte-containing sample from the subject. In another embodiment, step (i) may comprise isolating CD8+CD25+CD45RO−CD62L+CD127$^{lo}$ naïve Treg from a suitable lymphocyte-containing sample from the subject. In yet another embodiment, step (i) may comprise isolating CD8+CD25+CD45RO+ activated Treg or CD8+CD25+CD45RA− activated Treg from a suitable lymphocyte-containing sample from the subject. In still yet another embodiment, step (i) may comprise isolating CD8+CD25+CD45RO+CD62L+/−CD127$^{lo}$ activated Treg from a suitable lymphocyte-containing sample from the subject.

Preferably, step (iii) comprises isolating cells that co-express each of the cell markers CD8, CD25 and CD137 as well as one or more cell markers selected from the group of Treg cell markers consisting of CD39, CD45RO, CD73, CD127, CTLA-4 and Foxp3. More preferably, step (iii) comprises isolating CD8+CD25+CD137+ cells that also co-express the Treg cell markers CD39 and CD127.

Preferably, where CD127 is detected, the method comprises a CD127$^{lo}$ level of expression.

Preferably, the step of isolating antigen-specific CD8+ CD25+CD137+ Treg in the cultured sample occurs before a substantial number of cells present in the culture have divided in response to the antigen. Preferably, the antigen-specific Treg isolating step of the method is performed within about 24 to 96 hours of commencement of the culturing step. In some embodiments, the antigen-specific Treg isolating step is performed within about 40 to 44 hours of commencement of the culturing step. However, naïve Treg may require a longer time period to respond to antigen than activated Treg. Accordingly, in some embodiments, the antigen-specific Treg isolating step is performed within about 72 hours of commencement of the culturing step.

In some embodiments, the lymphocyte-containing sample may be a whole blood sample. Alternatively, the lymphocyte-containing sample may be a purified peripheral blood mononuclear cell sample. In some embodiments, the subject is human.

In a sixth aspect, the present invention provides a method of providing an expanded population of antigen-specific Treg the method comprising expanding in vitro the population of antigen-specific Treg isolated in accordance with the method of the third, fourth or fifth aspects of the invention.

Isolated antigen-specific Treg may be expanded using expansion protocols well known to persons skilled in the art, for example, by culturing in the presence of IL-2 and TCR stimulators (eg anti-CD28 or antigen), and/or in the presence of irradiated CD32+ L cells, to obtain the desired quantity of the antigen-specific Treg. The expanded antigen-specific Treg population, or cells thereof, may be administered (eg by infusion) to the subject from which the naïve Treg or activated Treg were obtained. The administered antigen-specific Treg can thus be used to treat conditions or diseases selected from the group consisting of T cell mediated diseases, autoimmune diseases, allergic diseases, immunoinflammatory diseases, infectious diseases, and allograft rejection. More particularly, the expanded antigen-specific Treg can thus be used to treat conditions or diseases selected from the group consisting of multiple sclerosis, type 1 diabetes, psoriasis, myasthenia gravis, rheumatoid and juvenile idiopathic arthritis, immunodysregulation, IPEX, WAS, APS, ALPS, and graft-versus-host disease.

In a seventh aspect, the present invention provides a method of cell therapy comprising administering antigen-specific Treg isolated according to the method of the third, fourth or fifth aspects of the invention to a subject.

Additionally, in an eighth aspect, the present invention provides a method of cell therapy comprising administering the antigen-specific Treg population expanded according to the sixth aspect of the invention to a subject.

In order that the nature of the present invention may be more clearly understood, preferred forms thereof will now be described with reference to the following non-limiting examples.

EXAMPLES

Example 1

Antigen Stimulation and Cell Identification and Isolation

Materials and Methods

Reagents

The antigens used were cytomegalovirus (CMV) lysate (22), mycobacterial antigen lysates (Mycobacterial tuberculosis (MTB) or Mycobacterial Avium intracellular complex (MAI), CSL, Melbourne, Australia), CMV-peptide (P1) (23, 24). *Staphylococcal* enteroantigen B (SEB) (Sigma-Aldrich Co., St Louis, Mo., United States of America) was used as a mitogen.

The monoclonal antibodies (mAbs) used were anti-CD3-PerCP-Cy5.5, anti-CD4-PE-Cy7, anti-CD45RO-FITC, anti-CD25-APC, anti-CD134-FITC, anti-CD134-PE and anti-Foxp3 (clone 259D) (all from Becton-Dickinson, San Jose, Calif., United States of America); anti-CD45RO-ECD (Beckman Coulter, Hialeah, Fla., United States of America); CD127-PE (Immunotech, Marseille, France); anti-CD127-Pacific Blue and anti-Foxp3-APC (clone PCH101) (eBiosciences, San Diego, Calif., United States of America); and CD39-PE (Serotec, Oxford, UK). All antibodies were used according to the manufacturer's directions.

In Vitro Cell Stimulation with Soluble Antigen

Samples were either whole blood or freshly isolated peripheral blood mononuclear cells (PBMCs) as stated below. PBMCs were isolated using standard techniques. Samples were stimulated in vitro for 24 to 44 hours, except for stimulation of sorted naïve Treg which were stimulated for 72 hours, at 37° C. with 5-10 μg/ml CMV lysate, mycobacterial antigen (MTB or MAI) lysates, CMV-peptide (P1) or SEB as described below.

Flow Cytometry

Staining of CD4+ T cell subsets was performed on whole blood or on freshly isolated PBMC samples following antigen stimulation. Cells were stained as previously described (17) and analysed on a three-laser LSR II flow cytometer (Becton-Dickinson). A minimum of 100,000 events, were collected and analysis was performed using FlowJo software (Treestar, San Carlos, Calif., United States of America).

Example 2

Identification of CD4+CD25+CD134+Foxp3+ Antigen-specific Treg from Whole Blood

Foxp3 is an accepted marker of Treg. It was investigated whether antigen-specific CD4+ Treg could be identified in whole blood by detecting the co-expression of CD4, CD134, CD25 and Foxp3 following in vitro stimulation with antigen Materials and Methods Whole blood from two healthy controls (donor 1 and donor 2), who were known to have active immune responses to MAI, MTB or CMV was stimulated in vitro with no antigen, CMV, MTB or MAI lysates as described in Example 1. In a second experiment, whole blood from donor 1 was stimulated with no antigen, CMV-P1 antigen or SEB mitogen (as a positive control) for 24 to 40 hours as described in Example 1.

The cells were then stained with the combination of mAbs consisting of anti-CD3, anti-CD4, anti-CD25, anti-CD134 and anti-Foxp3 antibodies. Cell staining was analysed on a three-laser LSR II flow cytometer (Becton-Dickinson). Antigen-specific Treg were gated as CD3+CD4+CD25+CD134+Foxp3+.

Results

The results shown in FIG. 1A demonstrate CD134 expression on CD4+CD25+ cells specific for CMV, MTB or MAI lysates from whole blood from two donors (top panel for each donor). FIG. 1A (bottom panel for each donor) shows Foxp3 expression on CD4+CD25+CD134+ subsets (shown in top panel) stimulated with no antigen, or CMV, MTB or MAI lysate antigens. Two different clones of Foxp3 monoclonal antibodies (PCH101 and 259D) were used and the results were comparable.

Approximately 7% and 57% of the CMV-specific CD4+CD25+CD134+ cells expressed Foxp3 for donor 1 and 2, respectively. Similarly, 57% of MTB-specific CD4+CD25+CD134+ cells expressed Foxp3 (for both donors); and 68% and 63% MAI-specific CD4+CD25+CD134+ expressed Foxp3 for donor 1 and 2, respectively.

The results shown in FIG. 1B (upper panel) demonstrate CD134 expression on CD4+CD25+ cells stimulated with no antigen, CMV-peptide (P1) or SEB (as a positive control) in whole blood. The results in FIG. 1B (lower panel), show Foxp3 expression on the CD4-CD25+CD134+ subset. Following stimulation of whole blood with SEB, 57% of the CD4+CD25+CD134+ cells were Foxp3+ demonstrating that Treg specifically express CD134 in response to TCR stimulation; and following stimulation with CMV-peptide (P1), 62% of the CD4+CD25+CD134+ cells were Foxp3+.

Discussion

Together, the results show that detecting the co-expression of CD4, CD25, CD134 and Foxp3 using a combination of mAbs allows for the accurate identification of antigen-specific Treg after in vitro stimulation with a target antigen.

Example 3

Isolation of CD4+CD25+CD39+CD134+ Viable Antigen-Specific Treg from Whole Blood

Detection of Foxp3 requires cell permeabilisation, which is problematical when it is desirable to have live cells following cell staining. CD39 has recently been reported to be a useful alternative marker for detecting Treg. In this example, the present applicant investigated whether antigen-specific CD4+ Treg could be identified in whole blood following in vitro stimulation with antigen by detecting the co-expression of CD4, CD25, CD134 and CD39.

Materials and Methods

Whole blood from donor 1 was stimulated with no antigen, CMV-P1 antigen or SEB mitogen (as a positive control) for 24 hr as described in Examples 1 and 2. The cells were then stained with the monoclonal antibodies consisting of anti-CD3, anti-CD4, anti-CD39, anti-CD25, anti-CD134 and anti-Foxp3 as described in Examples 1 and 2. CD3+CD4+ cells were gated.

Results

Figure 2:
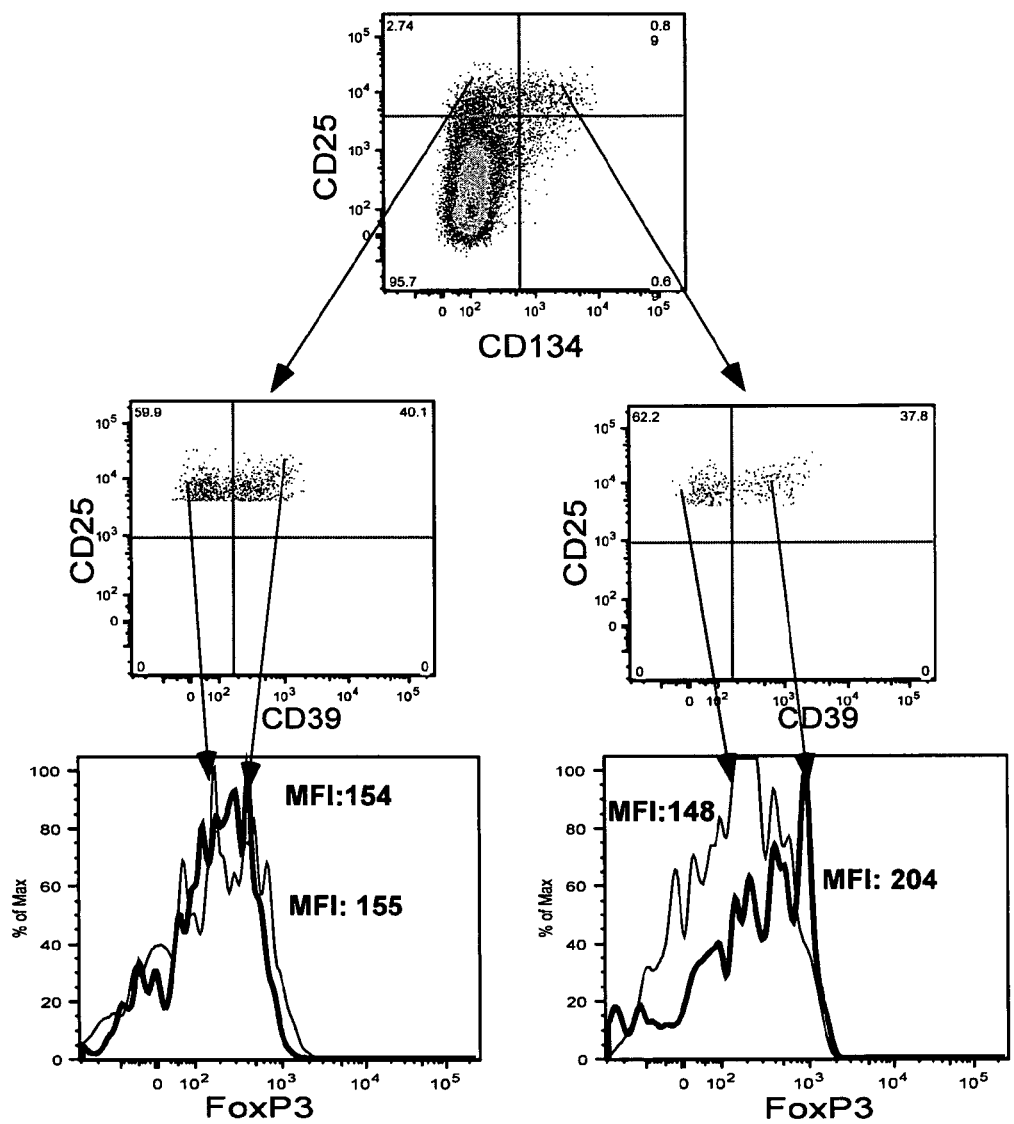
FIG. 2 provides FACS analysis plots of Foxp3 expression in CD39$^+$ and CD39$^-$ subsets of antigen-specific CD4$^+$CD25$^+$CD134$^+$ cells and CD4$^+$CD25$^+$CD134$^-$ antigen non-specific T cells and following antigen stimulation in vitro in whole blood samples for 24-40 hours.

The plots shown in FIG. 2 demonstrate that approximately 38% of CD4+CD25+CD134+ cells co-expressed CD39. Foxp3 expression on subsets of CD4+CD25+CD39+CD134+, CD4+CD25+CD39-CD134+, CD4+CD25+CD39+CD134- and CD4+CD25+CD39-CD134+ cells are shown in the histograms (bottom). Foxp3 was highly expressed in 90% of CD4+CD25+CD39+CD134+ cells compared to the CD4+CD25+CD39-CD134+ subset (MFI:204 and 148 respectively). However, Foxp3 expression was equivalent on CD134- (antigen non-specific) cells regardless of CD39 expression (i.e. CD4+CD25+CD134-CD39+or CD4+CD25+CD134-CD39- cells; MFI:154 and 155 respectively).

Discussion

The results show that CD39 is a useful marker for detecting antigen-specific Treg and that it is accordingly useful to include anti-CD39 in the combination of monoclonal antibodies with anti-CD4, anti-CD25 and anti-CD134 to isolate viable antigen-specific Treg. Approximately 90% of CD4+CD25+CD134+CD39+ were Foxp3 positive, as compared to CD4+CD25+CD134+CD39-, CD4+CD25+CD134-CD39+ and CD4+CD25+CD134-CD39- cells.

Example 4

Determining CD39 Expression on Naïve or Activated Treg

CD39 expression has been reported on Treg (18,19) but it has not been clarified whether CD39 expression is associated with naïve or activated Treg or both. CD39 expression was investigated on a naïve Treg population gated as CD25+CD45RO-CD62L+ CD127$^{lo}$ and activated memory Treg population gated as CD25+CD45RO+CD62L+/- CD127$^{lo}$, which were isolated from whole blood without antigen stimulation. CD62L is also known as L-selectin, which is expressed on naïve T cells which have not yet encountered a specific antigen, but which decreases during cell activation. The term "CD62L+/-" describes a cell population that consists of cells with all levels of CD62L expression.

Materials and Methods

Reagents and Cells

Peripheral blood mononuclear cells (PBMCs) were purified from whole blood collected from a healthy donor. The monoclonal antibodies (mAbs) used were anti-CD3-Percp-Cy5.5, anti-CD4-PE-Cy7, anti-CD25-APC, anti-CD39-PE, anti-CD45RO-ECD, anti-CD62L-APC-Cy7 (eBiosciences) and anti-CD127-Pacific Blue. All antibodies were used according to the manufacturer's instructions.

FACS Analysis

The PBMCs were stained with a combination of mAbs consisting of anti-CD3, anti-CD4, anti-CD25, anti-CD39, anti-CD45RO, anti-CD62L and anti-CD127 as described above. Cell staining was analysed on a three-laser LSR II flow cytometer (Becton-Dickinson).

Results and Discussion

Figure 3:
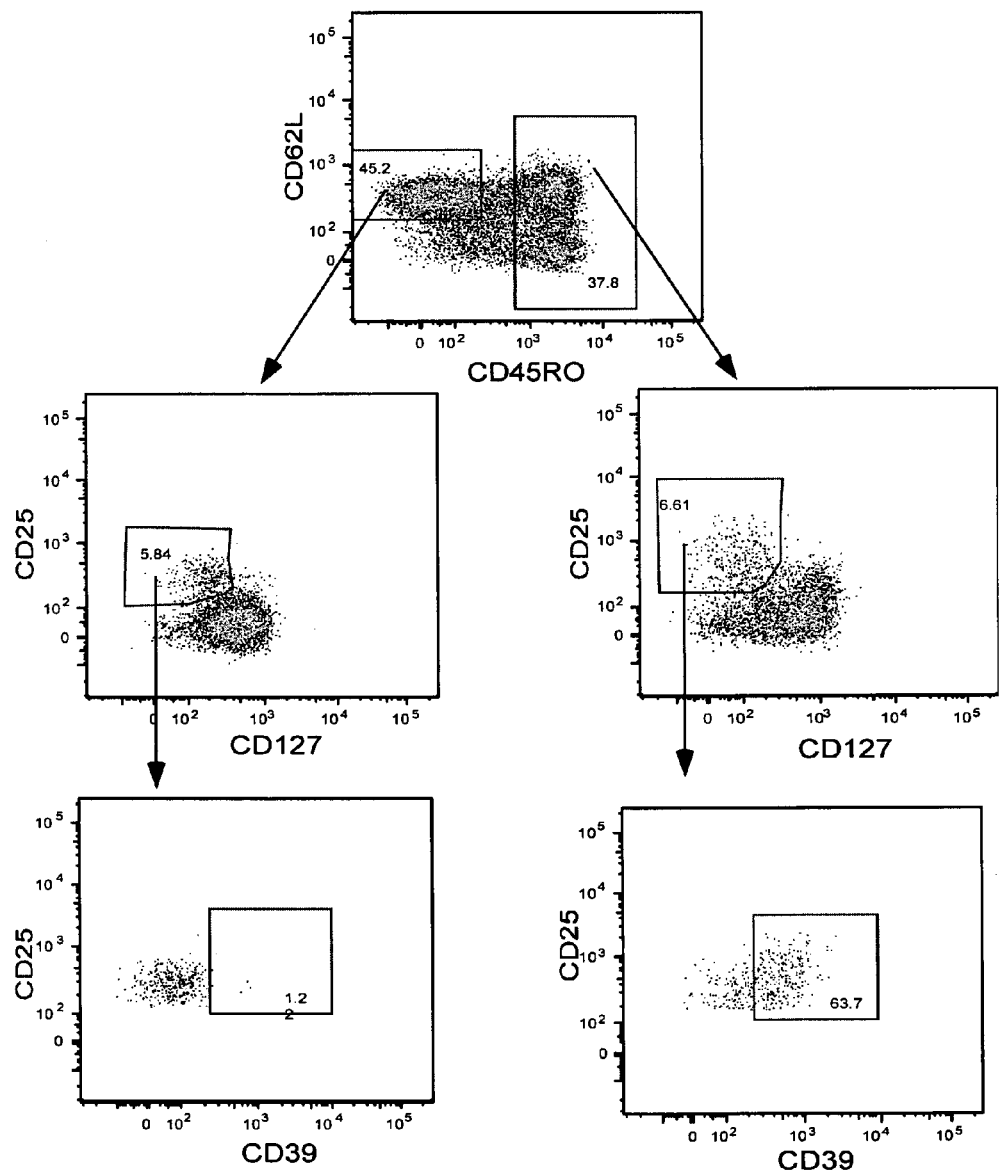
FIG. 3 provides FACS analysis plots comparing CD39 expression on naïve Treg (CD25$^+$CD62L$^+$CD45RO$^-$CD127$^{lo}$) and activated Treg (CD25$^+$CD62L$^{+/-}$CD45RO$^+$ CD127$^{lo}$) in peripheral blood mononuclear cells (PBMCs) from a healthy donor confirming CD39 is expressed on activated Treg.

CD39 expression was observed for activated Tregs ($CD25^+CD45RO^+CD62L^{+/-}$ $CD127^{lo}$) but not for naïve Tregs ($CD25^+CD45RO^-CD62L^+CD127^{lo}$) as shown in FIG. 3. This confirms that CD39 expression is associated with the activation of Treg. As activation of Treg is associated with stimulation of the cell by a specific antigen, this result indicates that Treg express CD39 after stimulation with a specific antigen.

Example 5

Investigating Function of $CD4^+CD25^+CD127^{lo}$ $CD134^+$ Antigen-Specific Treg $CD4^+CD25^+CD134^+$ T cells, following antigen stimulation in vitro, have previously been shown to be antigen-specific T cells; and $CD4^+CD25^+CD127^{lo}$ T cells have previously been shown to be Treg. This Example investigated whether $CD4^+CD25^+CD127^{lo}CD134^+$ T cells could be shown to suppress proliferation of responder T cells using a suppression assay.

Materials and Methods

A standard suppression assay can be used to determine if Treg are capable of suppressing the proliferation of responder cells (naïve $CD4^+$ Treg). The suppression assay used in this Example was performed as described in Example 10, except that in the present Example, the "suppressor" sample was PBMCs that have been isolated from Donor 1 (known to have a CMV response) and antigen stimulated with CMV-P1 peptide for 44 hr as described above. $CD4^+$ T cells were isolated using a commercial kit (dynal beads, Invitrogen) in order to obtain pure population of $CD4^+$ T cells excluding the majority of $CD8^+$, B cells and monocytes. The $CD4^+$ cell isolation step advantageously facilitates faster cell sorting, minimising the time that cells are removed from the culturing environment. The bead-isolated $CD4^+$ T cells were stained with anti-CD4, anti-CD25, anti-CD39, anti-CD127, and anti-CD134 antibodies and then sorted by flow cytometry (FACS) to obtain a $CD4^+CD25^+CD127^{lo}CD134^+$ CD39+ antigen-specific Treg population, as well as $CD4^+CD25^+CD127^{lo}CD134^-CD39^+$, $CD4^+CD25^+CD127^{lo}CD134^-CD39^-$ or $CD4^+CD25^+CD127^{lo}CD134^+CD39^-$ non antigen-specific cells. $CD4^+CD25^-CD127^+$ responder cells were isolated in parallel from fresh PBMCs, which were not stimulated with CMV-P1.

Results and Discussion

Freshly isolated Treg can be tested for suppressive function by mixing sorted Treg "suppressor" cells with an equal number of naïve "responder" $CD4^+$ cells, in the presence of antigen presenting cells and anti-CD3 (to polyclonally stimulate the TCR of T cells) or a specific antigen for 72 hr. The proliferation of responder cells is measured as a read-out. In this Example, the assay was adapted to determine if it was suitable for investigating suppression by antigen-specific Treg which were obtained by culturing PBMCs in vitro for 44 hr in the presence of antigen, and then sorted to be $CD4^+CD25^+CD39^+CD127^{lo}CD134^+$ prior to setting up the assay.

This adapted assay did not successfully show the suppressive function of antigen-specific Tregs (data not shown). This is likely to be because the assay is a technically difficult due to a number of factors, including: i) antigen-specific T cell response towards the CMV-peptide P1 used in the model is not very large compared to the polyclonal activation of all T cells using anti-CD3, for example, and therefore differences in the proliferation of responder cells alone or in the presence of $CD4^+CD25+CD39^+CD127^{lo}CD134^+$ Treg is difficult to detect; and ii) antigen-specific Tregs may proliferate in parallel to the responder cells, which makes the read-out of responder proliferation detection alone problematical; and notably, iii) antigen-specific Tregs (contained in PBMCs) may be exhausted as they were cultured for 44 h with CMV-P1 and responded by up-regulating CD25 and CD134 at which point they were sorted and cultured for a second time with sorted naïve responder cells (isolated from fresh PBMCs which have not been stimulated and cultured for 44 hrs), and it was during this second incubation that the ability to suppress the proliferation of the responders was investigated.

Accordingly, alternative techniques of determining whether the antigen-specific Treg have a suppressive nature, such as investigating the suppressive ability of a more heterogeneous population of cells which contains the $CD4^+CD25^+CD134^+$ antigen-specific Treg population (as described in example 10) or considering expression patterns of immunological marker genes by real-time PCR as described in Example 6.

Example 6

Comparing Expression of Genes in Antigen-Specific Treg ($CD4^+CD25^+CD39^+CD134^+$), Non-Antigen Specific Cells Including Naïve Treg Cells ($CD4^+CD25^+CD39^{+/-}CD134^-$), Antigen Specific Non-Treg T Cells ($CD4^+CD25^+CD39^-$ $CD134^+$) and Non-$CD4^+$ Cells by Real-Time PCR The mRNA expression pattern of Foxp3, T-bet, Gata3, retinoic acid-related orphan receptor (ROR)γt, TGF-β and IL-10 genes was examined in antigen-specific $CD4^+CD25^+CD39^+CD134^+$ Treg and was compared to the mRNA expression pattern in other cell populations to investigate whether $CD4^+CD25^+CD39^+CD134^+$ cells express genes that are associated with immune response suppression that is characteristic of Treg. Treg have previously been shown to express high levels of Foxp3 (25-27). TGF-β At least two different subsets of inducible Treg have been reported, among them, T regulatory type 1 (TR1) cells that produce high levels of interleukin-10 (IL-10) (3); and a subset of inducible $Foxp3^+CD4^+CD25^+$ Treg which can be generated in vitro from $CD4^+CD25^-$ T cells in the presence of transforming growth factor-β (TGF-β) (4). Accordingly, expression of Foxp3, TGF-β and IL-10 are all considered to be markers of Treg function. TGF-β facilitates the suppressive function of Treg (28). Additionally, Treg express low levels of T-bet and Gata-3, which are transcription factors associated with T helper1 (Th1) cells and T helper2 (Th2) cells, respectively (29). IL-10 was investigated as it is associated with suppressing immune responses (31); while RORγt is a transcription factor associated with Th17 cells (reviewed in 30).

Materials and Methods

Reagents and Cell Stimulation

PBMCs were purified from whole blood collected from a healthy donor. PBMCs were stimulated with P1 for 44 hr and the cells were then stained with the following monoclonal antibodies (mAbs): anti-CD3-percpCy5.5, anti-CD4-PE-Cy7, anti-CD25-APC, anti-CD39-FITC, anti-CD127-Pacific-Blue and anti-CD134⁻PE. All antibodies were used according to the manufacturer's instructions.

FACS Isolation of Cells

The cultured PBMCs were stained with a combination of mAbs consisting of anti-CD3, anti-CD4, anti-CD25, anti-CD39, and anti-CD134 as described above. Cells were then sorted, using a FACS ARIA cell sorter (Becton-Dickinson) so that cells were separated into an antigen-specific Treg population ($CD4^+CD25^+CD39^+CD134^+$), antigen-specific non-Treg ($CD4^+CD25^+CD39^-CD134^+$), non-antigen specific cells $CD4^+$ T cells including naïve Treg ($CD4^+CD25^+CD39^+CD134^-$) and non-antigen specific $CD4^+$ T cells ($CD4^+CD25^+CD39^-CD134^-$), and non-$CD4^+$ cells (which includes $CD8^+$ T cells, B cells, monocytes and NK cells) as a negative control. Sorted cells were stored in TRIZOL until RNA extraction was performed.

Real-Time Polymerase Chain Reaction (PCR)

Real-time PCR was performed using a standard technique (32) to quantify the mRNA expression level of the following genes: β-actin (house keeping gene), Foxp3, T-bet, Gata3, RORγt, TGF-β and IL-10. IL-10 was amplified using primers and conditions from Sigma-Aldrich. The variables for Tbet, GATA3, RORγt, Foxp3, β-actin, TGF-β and IL-10 are described in Table 1.

TABLE 1

Real-time PCR conditions

| Primer | Genbank Accession No. | Con (μM) | Annealing Temperature | Product (bp) |
|---|---|---|---|---|
| Tbet Forward | NM_013351.1 | 20 | 60 | 204 |
| Tbet Reverse | NM_013351.1 | 20 | 60 | 204 |
| GATA3 Forward | NM_001002295.1 | 20 | 60 | 130 |
| GATA Reverse | NM_001002295.1 | 20 | 60 | 130 |
| RORγt Forward | NM_001001523.1 | 30 | 59.2 | 85 |
| RORγT Reverse | NM_001001523.1 | 30 | 59.2 | 85 |
| Foxp3 Forward | NM_014009.3 | 20 | 60 | 67 |
| Foxp3 Reverse | NM_014009.3 | 20 | 60 | 67 |
| β-actin Forward | NM_001101.2 | 10 | 60 | 295 |
| B-actin Reverse | NM_001101.2 | 10 | 60 | 295 |
| TGFβ1 Forward | NM_014009.3 | 20 | 60 | 130 |
| TGFβ1 Reverse | NM_001101.2 | 10 | 60 | 130 |
| IL-10 Forward | NM_000584 | 10 | 60 | 170 |
| IL-10 Reverse | NM_000584 | 10 | 60 | 170 |

Results and Discussion

Figure 4:
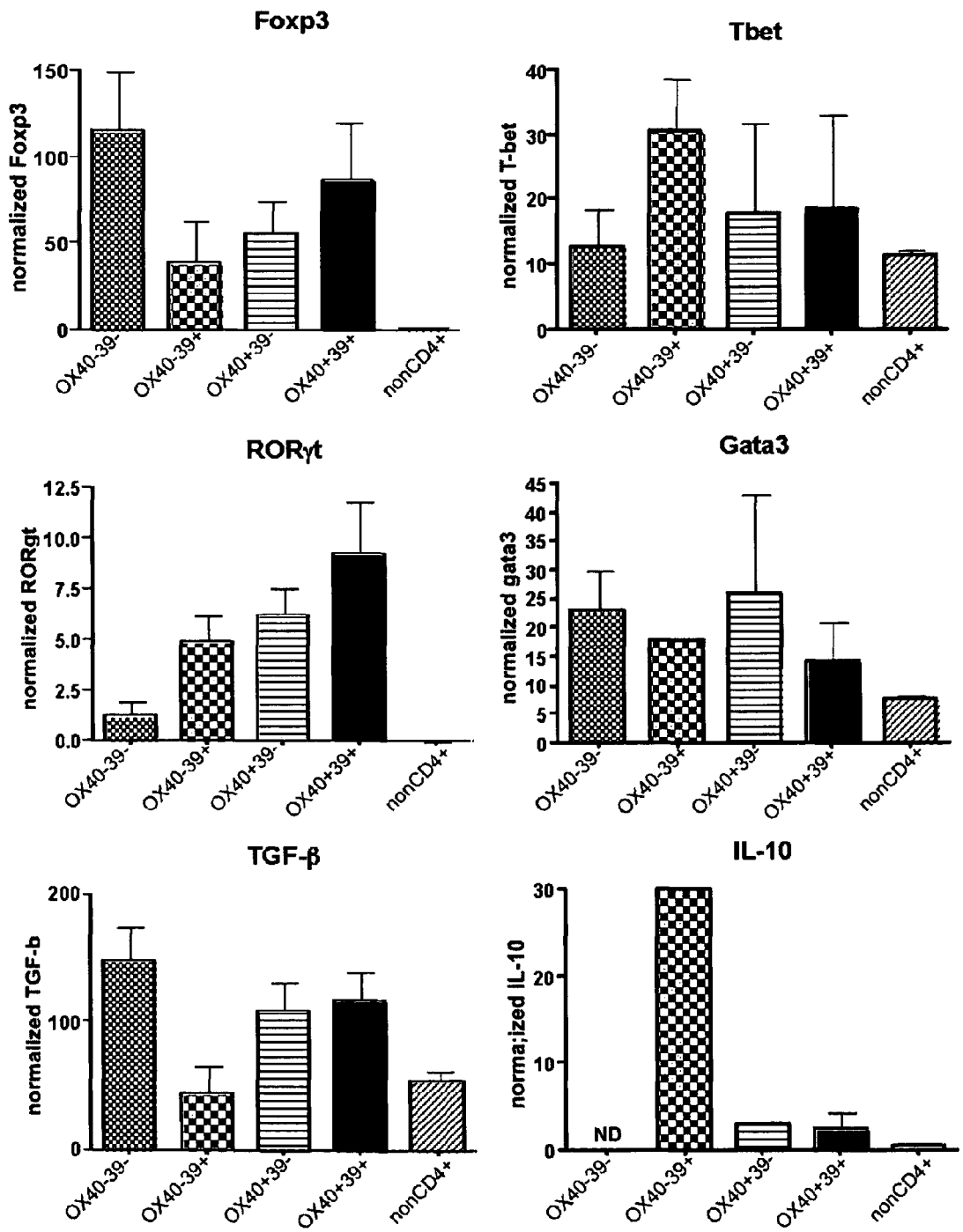
FIG. 4 provides quantitative real-time polymerase chain reaction (PCR) plots demonstrating mRNA expression patterns of Foxp3, T-bet, RORγt, Gata3, TGF-β and IL-10 genes in PBMCs that had been antigen stimulated and then sorted into populations of antigen-specific Treg (ie CD4$^+$CD25$^+$CD39$^+$CD134$^+$ cells labelled "OX40+39+"), antigen-specific non-Treg (CD4$^+$CD25$^+$CD39$^-$ CD134$^+$ cells labelled "OX40+39$^-$"), non-antigen specific cells CD4$^+$ T cells including naïve Treg (ie. CD4$^+$CD25$^+$CD39$^+$CD134$^-$ cells labelled "OX40$^-$39$^+$"), non-antigen specific CD4$^+$ T cells (ie CD4$^+$CD25$^+$CD39$^-$CD134$^-$ cells labelled OX40$^-$39$^-$), and non-CD4$^+$ cells (ie CD4$^+$ cells, which includes CD8$^+$ T cells, B cells, monocytes and NK cells, labelled "non-CD4$^+$") as a negative control.

Quantitative Real-Time PCR results demonstrated fold-differences in mRNA expression patterns between the cell populations examined after normalisation to β-actin as shown in FIG. 4. The $CD4^+CD25^+CD39^+CD134^+$ antigen-specific Treg expressed high levels of Foxp3 and TGF-β (markers of Treg function) but lower levels of T-bet and Gata-3 (markers for Th1 and Th2 cells, respectively). This subset also expressed lower levels of IL-10, which indicates that the antigen-specific Treg resembles a Th3-like Treg.

The $CD4^+CD25^+CD39^-CD134^-$ cell population expresses the highest level of Foxp3 as it includes natural Treg as shown previously (17). Of note, antigen-specific $CD4^+CD25^+CD39^+CD134^+$ Treg surprisingly express a high level of ROR-γt, which was previously thought to be specific for Th17 cells. However, it has recently been reported that Treg could express ROR-γt in certain conditions (33).

Example 7

$CD4^+CD25^+CD134^+Foxp3^+$ Antigen-Specific Treg are Contained within the $CD4^+CD25^+CD39^+CD127^{lo}$ Treg Population Materials and Methods Peripheral blood was obtained from a healthy donor. P1-CMV peptide antigen (10 μg/ml) was added to 200 μl whole blood samples in 24 well culture plates and incubated for 40 to 44 h. A combination of antibodies was then added to samples, consisting of anti-CD3 PercpCy5.5, anti-CD4-Alexa 700, anti-CD25-biotin+streptavidin 655Qdot, anti-CD39-FITC, anti-CD134-PE and anti-Foxp3-APC, and incubated for 15 min at room temperature. The red blood cells were then lysed using a lysis buffer (Becton-Dickinson) and the cells washed and fixed with PBS 0.5% paraformaldehyde solution. Cells were analysed on a three-laser LSR II flow cytometer (Becton-Dickinson). A minimum of 100,000 events were collected and analysis was performed using FlowJo software. The results shown in FIG. 5 have been gated for $CD3^+CD4^+$ cells.

Results and Discussion

Figure 5:
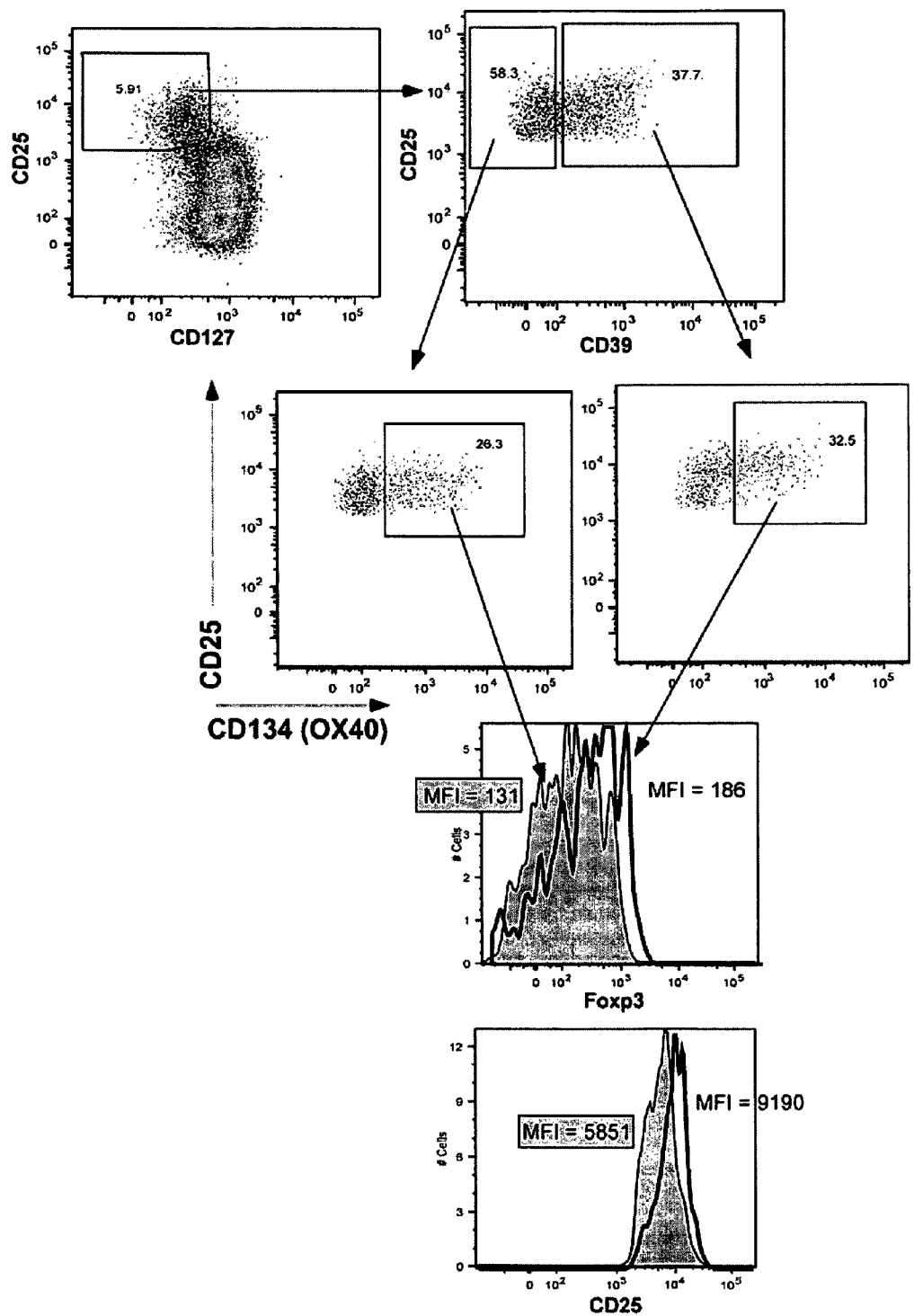
FIG. 5 provides FACS analysis plots of antigen stimulated CD3+CD4$^+$ gated cells showing that following antigen stimulation the CD4$^+$CD25$^+$CD39$^+$CD127$^{lo}$ Treg population contain an antigen-specific CD4$^+$CD25$^+$CD134$^+$Foxp3$^+$ Treg population, (top left) gating of cells for CD25$^+$CD127$^{lo}$, (top right) gating of CD25$^+$CD127$^{lo}$ for CD39, (middle left) gating of CD25$^+$CD127$^{lo}$CD39$^-$ or (middle right) CD25$^+$CD127$^{lo}$CD39$^+$ cells for CD134, and (bottom) histograms showing Foxp3 expression or CD25 expression (extreme bottom) on the CD4$^+$CD25$^+$CD39$^+$CD134$^+$CD127$^{lo}$ and CD4$^+$CD25$^+$CD39$^-$CD134$^+$CD127$^{lo}$ (shaded) populations.

As shown in FIG. 5, the $CD4^+CD25^+CD134^+Foxp3^+$antigen-specific Treg subset are contained within the $CD4^+CD25^+CD39^+CD127^{lo}$ Treg subset following stimulation with antigen. In fact, 32.5% of $CD4^+CD25^+CD39^+CD127^{lo}$ cells were also $CD134^+$. $CD4^+CD4^+CD25^+CD39^-CD127^{lo}$ cells also contained a $CD134^+$ subset, but these cells had lower Foxp3 expression ($CD4^+CD25^+CD39^-CD127^{lo}$ $CD134^+$ cells had a mean fluorescence intensity (MFI) of 131 compared to MFI=186 for $CD4^+CD25^+CD39^+CD127^{lo}CD134^+$ cells). Accordingly, the $CD4^+CD25^+CD134^+$ antigen-specific Treg population is likely to have higher purity when the cells are gated using two Treg markers, such that they are $CD39^+CD127^{lo}$. Interestingly, antigen-specific Treg population (eg $CD4^+CD25^+CD39^+CD127^{lo}CD134^+$ cells) showed a higher CD25 expression level (MFI=9190) than the non-specific Treg population (eg $CD4^+CD25^+CD39^+CD127^{lo}CD134^-$ cells) (MFI=5851). The higher expression level of CD25 demonstrates that the $CD4^+CD25^+CD39^+CD127^{lo}CD134^+$antigen-specific Treg are responding in response to stimulation with specific antigen.

Example 8

IL-2 and IFNγ Production by Antigen-Stimulated $CD25^+Foxp3^+$ Cells

Treg do not usually secrete IL-2 and IFN-γ (34). IL-2 and IFNγ expression was examined by intracellular staining in antigen-stimulated $CD4^+CD25^+Foxp3^+$ cells, which includes a subset of $CD4^+CD25^+CD39^+CD134^+$ antigen-specific Treg as shown in Example 9, to investigate whether these cells have Treg characteristics.

Materials and Methods

Cells

Whole blood was collected from healthy donors known to have a response to CMV.

FACS Antibodies

Anti-CD3-PercpCy5.5, anti-CD4-PECy7, anti-CD25-biotin (Immunotech, Marseille, France) +streptavidin 655QDot (Invitrogen), CD127-Pacific-Blue and anti-Foxp3-PE (Becton-Dickinson) monoclonal antibodies were used to stained for surface and intracellular markers as described below. Intracellular staining for IL-2 and IFN-γ was conducted using anti-IL-2-FITC (Becton-Dickinson) and anti-IFN-γ-APC (Becton-Dickinson) monoclonal antibodies in accordance with the manufacturer's instructions.

Antigens and Cell Stimulation

SEB or CMV lysate at 5 µg/ml, or CMV-P1 peptide or CMV-P3 peptide at 10 µg/ml, were used to antigen stimulate cells as described above. CMV-P3 peptide was used as a negative control as the donor was previously tested and was known not to specifically respond to CMV-P3. Antibodies directed against polyclonal TCR co-stimulatory molecules CD28 and CD49d (eg anti-CD28 and anti-CD49d) (Becton-Dickinson) were used at 5 µg/ml to stimulate cells for the cytokine expression to stimulate the cells for cytokine secretion as described previously (22).

500 µl of whole blood was aliquoted per well into a 24-well plate. SEB, CMV lysate or CMV-peptide (P1 or P3) antigens, or no antigen for the negative control, were added to the wells in the presence of anti-CD28 and anti-CD49d mAbs. The plates were incubated at 37° C. in a 5% $CO_2$ atmosphere for 2 hours. At this point, 10 µL of Brefeldin A (Sigma-Aldrich Co.) at 10 □g/mL was added to each of the wells, and the culture placed back at 37° C. 5% $CO_2$ for a further 4 hours. Finally, EDTA (Sigma-Aldrich Co.) was added to samples at a final concentration of 2 mM, and the plates were incubated at room temperature for 15 minutes, and the cells were stained as below.

Cell Staining

Cells were stained for surface and intracellular markers CD3, CD4, CD25 and Foxp3 as described above, and erythrocytes were lysed using a lysis buffer (BD Biosciences). Cells were then intracellularly stained for the presence of IL-2 and IFNγ as follows, samples were treated with FACSPerm solution (BD Biosciences) for 10 minutes, and were then washed and stained with anti-IL-2 and anti-IFNγ according to the manufacturer's instructions. Cell staining was analysed on a three-laser LSR II flow cytometer (Becton-Dickinson). Cells were gated as $CD3^+CD4^+CD25^+Foxp3^+$ Treg cells or $CD3^+CD4^+CD25^{+/-}Foxp3^-$ effector cells (as a positive control for cytokine expression).

Results and Discussion

Figure 6:
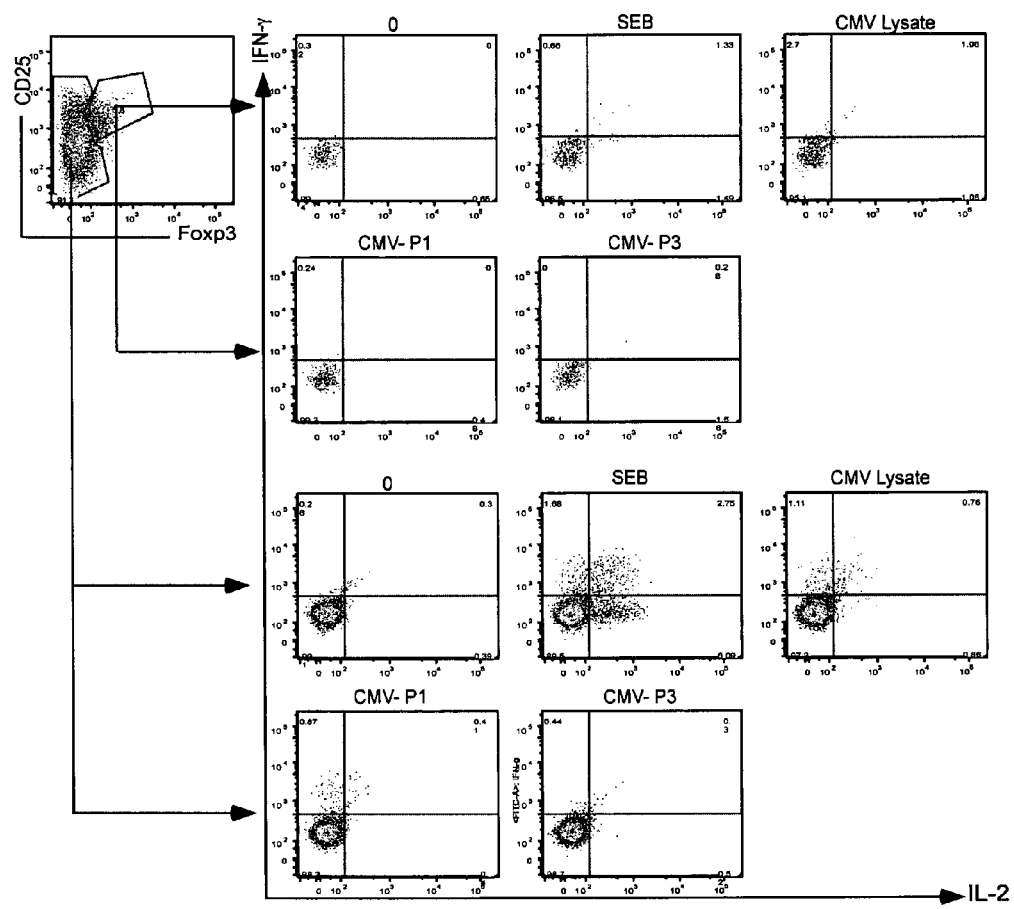
FIG. 6 provides FACS plots of IFNγ and IL-2 expression in antigen stimulated CD4$^+$CD25$^+$Foxp3$^+$ Treg which include the CD4$^+$CD25+CD39$^+$CD134$^+$ subset of antigen-specific Treg or in CD4$^+$CD25$^{+/-}$ Foxp3$^-$ cells as a positive control for cytokine expression.

The expression of IL-2 and IFNγ in $CD4^+CD25^+Foxp3^+$ Treg was investigated by flow cytometry using intracellular staining and the results are shown in FIG. 6. $CD4^+CD25^+Foxp3^+$ cells, which include the $CD4^+CD25^+CD39^+CD134^+$ subset of antigen-specific Tregs, do not produce IL-2 or IFN-γ following antigen stimulation. These results add to the observation that the population of $CD4^+CD25^+Foxp3^+$ cells, which contains $CD4^+CD25^+CD134^+Foxp3^+$ cells, function as Treg cells. Interestingly, these cytokines were secreted by non-Treg cells, gated as $CD4^+CD25^{+/-}Foxp3^-$. Staining for expression of CD39 and CD134 was not performed in this combination as the available fluorochrome combination for these antibodies did not permit it.

Example 9

Gating Strategy for Enriching for Foxp3+ Cells within Viable Antigen-Specific Treg Population Using Alternative Treg Markers While Foxp3 is thought to be the best marker for Treg cells, alternative markers are sought as cells must be permeabilised to be stained for Foxp3.

Materials and Methods

Whole blood was obtained from a healthy donor, and was stimulated with CMV-P1 for 44 hr as described above. Cells were then stained with the following antibodies anti-CD3-PercpCy5.5, anti-CD4PE-Cy7, anti-CD25biotin+streptavidin 655Qdot, anti-CD39-FITC, anti-CD134-PE and anti-Foxp3-APC as described above. Cell staining was analysed on a three-laser LSR II flow cytometer (Becton-Dickinson).

Results and Discussion

Figure 7:
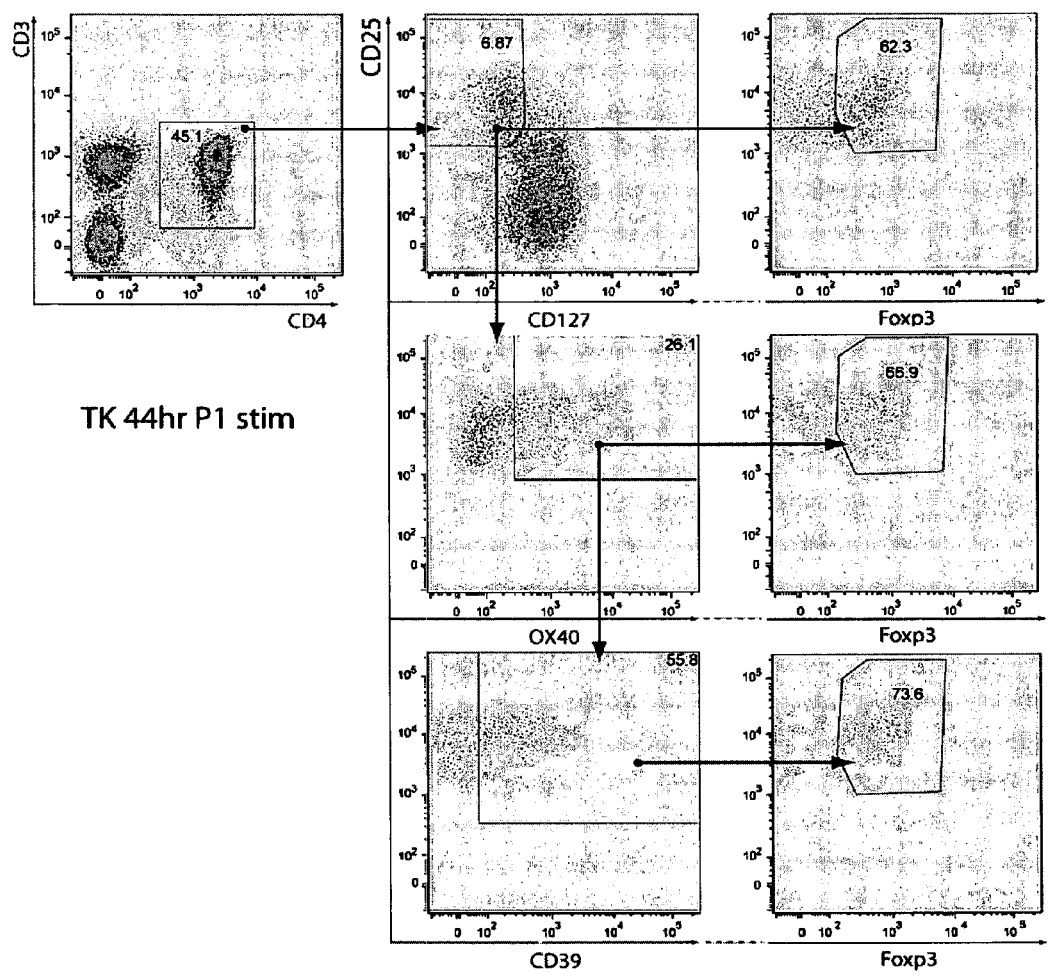
FIG. 7 provides FACS analysis plots of Foxp3 expression on in vitro antigen-stimulated CD4$^+$CD25$^+$CD127$^{lo}$ cells compared to CD4$^+$CD25$^+$CD127$^{lo}$ CD134$^+$ and CD4$^+$CD25$^+$CD39$^+$CD127$^{lo}$CD134$^+$ cells (CD134 is labelled as "OX40")

FIG. 7 shows a gating strategy for enriching a viable antigen-specific Treg population for Foxp3+ Treg. Antigen-specific $CD3+CD4^+CD25^+CD127^{lo}CD134^+$ cells are approximately 66.9% $Foxp3^+$. When these cells were also gated as being CD39+ (ie $CD3+CD4^+CD25^+CD39^+CD127^{lo}CD134^+$ cells), 73.6% of cells were $Foxp3^+$. Thus, the population of antigen-stimulated Treg with the phenotype $CD4^+CD25^+CD39^+CD127^{lo}CD134^+$ are advantageously enriched for FoxP3 expression.

Example 10

Suppressive Activity of $CD4^+CD25^+CD39^+CD127^{lo}$ Treg on Naïve "Responder" $CD4^+CD25^-CD127^{hi}$ T Cells The suppressive capability of a $CD4^+CD25^+CD39^+CD127^{lo}$ population, which includes a $CD4^+CD25^+CD134^+$ antigen-specific subset, was examined following antigen stimulation to investigate whether the population has Treg functionality.

Materials and Methods

Cell Isolation

PBMCs were purified from peripheral blood obtained from a healthy donor. A population of $CD4^+CD25^+CD39^+CD127^{lo}$ Treg (ie "CD39+ suppressor cells"), a population of $CD4^+CD25^+CD39^-CD127^{lo}$ Treg (ie "CD39- suppressor cells"), and a population of population of naïve $CD4^+CD25^-CD127^{hi}$ "responder" T cells were isolated by FACS using a similar technique as described above. Non-T cell PBMCs were negatively depleted using magnetic anti-CD3 beads (Dynal, Invitrogen) and were collected and used as antigen presenting cells (APC). The APCs were irradiated before use (3000 rad).

Suppression Assay $2 \times 10^4$ responder cells and $2 \times 10^4$ suppressor cells (i.e. responder:suppressor cells in a 1:1 ratio) were placed with $5 \times 10^4$ irradiated antigen presenting cells (APCs) in medium consisting of RPMI 1640 supplemented with 10% heat inactivated human AB serum (Sigma-Aldrich Co.), 2 mM L-glutamine (Invitrogen), 100 U/mL penicillin (Invitrogen), and 100 □g/mL streptomycin (Invitrogen) along with either 0.25 ug/mL anti-CD3 (clone Hit3a, PharMingen) as a polyclonal stimulator or 10 ug/mL CMV pp65 P1 peptide (Mimotopes) as antigen. Wells containing responder:responder cells (i.e. containing $4 \times 10^4$ responder cells and no suppressor cells) were set up in parallel as a positive control. Wells containing an anti-CD3 mAb to induce polyclonal stimulation of the TCR was set up as a positive polyconal suppression control. Each condition was repeated in triplicate, except for samples containing CD39+ suppressor cells:responder cells, which were repeated in duplicate. The assay was conducted in 96-well U-bottom culture plates. After 72 h of culture, cells were pulsed with [$^3$H] tritiated thymidine for 16 h before harvesting. Proliferation of responder cells was measured be incorporation of tritiated thymadine as counts per minute (CPM) on a TopCount β-counter (PerkinElmer) and suppression was calculated by dividing the average CPM of the suppressor:responder wells by the average CPM of the responder:responder wells.

Cytokine Detection

Before adding thymidine, 100 µl of supernatant from each well was collected for measurement of cytokines including IFNγ (indicative of active T cell responses) and IL-10 (indicative of general suppression of immune responses) using a Th1/Th2 bead array cytokine kit from Becton Dickinson, according to the manufacturer's instructions.

Results and Discussion

Figure 8:
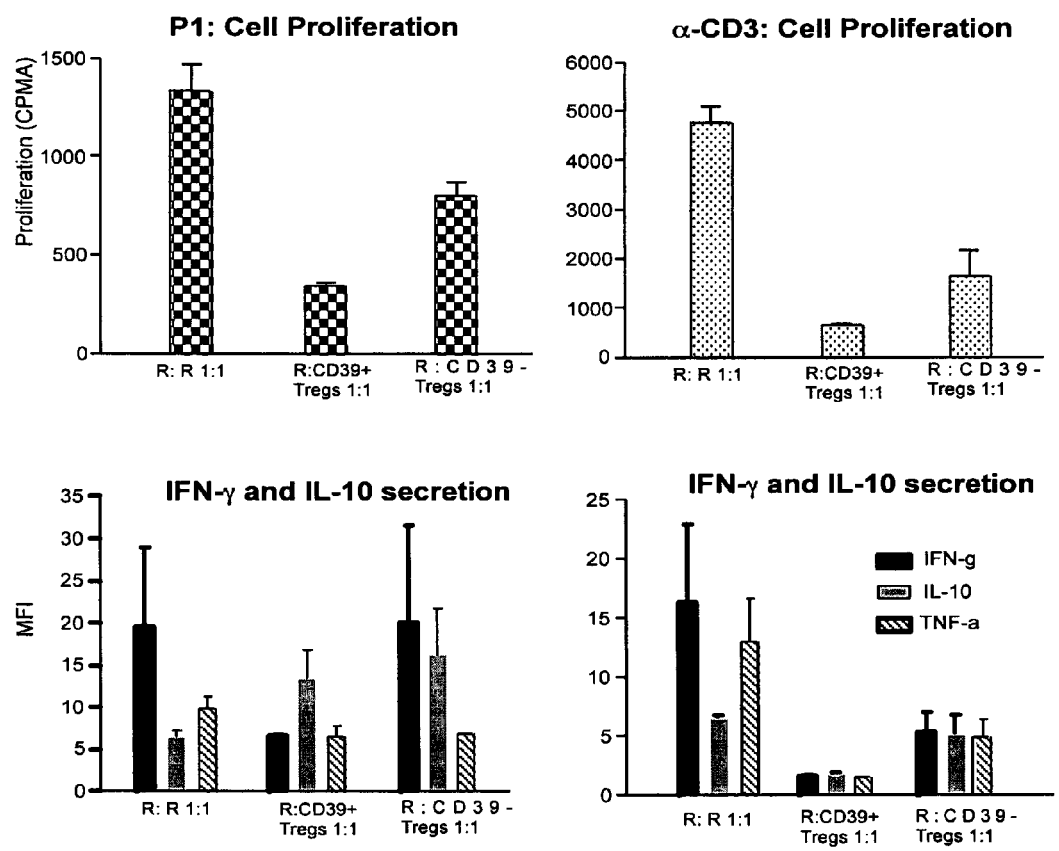
FIG. 8 provides plots showing (top) suppression of proliferation of responder T cells (labelled "R") by CD4$^+$CD25+CD39$^+$CD127$^{lo}$ suppressor cells (labelled "CD39$^+$ Treg") or by CD4$^+$CD25$^+$CD39$^-$CD127$^{lo}$ suppressor cells (labelled "CD39$^-$ Treg"), following stimulation with either CMV pp65 P1 antigen (labelled "P1", left) or with anti-CD3 (right), and (bottom) levels of IFNγ, IL-10 and TNF-α secreted into each of the cell supernatants during the assay.

The results of the suppression assay are shown in FIG. 8 (top), and the levels of IFNγ and IL-10 in cell supernatants shown in FIG. 8 (bottom). The CD4$^+$CD25$^+$CD39$^+$CD127$^{lo}$ antigen stimulated population, which contains CD4$^+$CD25$^+$CD39$^+$CD127$^{lo}$CD134$^+$ antigen-specific Treg enhanced suppression of proliferation of the responder cells compared to the CD4$^+$CD25$^+$CD39$^-$CD127$^{lo}$ antigen-stimulated population. Further, IFNγ expression was suppressed in the CD4$^+$CD25$^+$CD39$^+$CD127$^{lo}$ population, compared to the CD4$^+$CD25$^+$CD39$^-$CD127$^{lo}$ population, indicating that the CD4$^+$CD25$^+$CD39$^+$CD127$^{lo}$ population suppressed T cell activation more efficiently than the CD4$^+$CD25$^+$CD39$^-$CD127$^{lo}$ population.

Example 11

Isolation of Pure Populations of Viable Antigen-Specific CD4$^+$ Treg that are Foxp3$^+$ To investigate whether antigen-specific CD4$^+$ Treg can be isolated in relatively pure populations, PBMCs were first sorted into a naïve Treg population (CD4$^+$CD25$^+$CD45RO$^-$CD127$^{lo}$), an activated Treg population (CD4$^+$CD25$^+$CD45RO$^+$CD127$^{lo}$) and a naïve CD4$^+$CD25$^-$ T cell population. The sorted populations were then cultured with antigen in vitro, and re-sorted to determine the percentage of CD4$^+$CD25$^+$CD134$^+$cells that were Foxp3$^+$. Naïve CD4$^+$CD25$^+$CD45RO$^-$CD127$^{lo}$ Treg have previously been shown to express a uniformly high level of Foxp3 (17).

Materials and Methods

Initial Cell Sorting

Unstimulated PBMCs (2.5 to 5×10$^7$) from healthy controls were stained with a combination of anti-CD4-PE-Cy7, anti-CD25-APC, anti-CD127-Pacific Blue and anti-CD45RO-ECD mAbs. FACS cell sorting was performed so that cells were separated into populations of naïve Treg (CD4+CD25$^+$CD127$^{lo}$CD45RO$^-$), activated Treg (CD4+CD25$^+$CD127$^{lo}$CD45RO$^+$) and naïve T cells (CD4+CD25$^-$CD127$^{hi}$) using an ARIA cell sorter (Becton-Dickinson).

In Vitro Cell Stimulation with Soluble Antigen

Each of the sorted populations was cultured with CMV-P1 peptide at a concentration of 10 µg/ml for 3 days as described in Example 1. Specifically, the naïve Treg and activated Treg populations were stimulated for 44 hr, and the naïve T cells were stimulated for 72 hr, as these cells require more time to upregulate CD134 expression (nb. an aliquot was checked for CD134 expression at 44 hr; data not shown).

Isolation of Pure Population of Antigen-Specific Treg by FACS Sorting

Following culturing with antigen, each cultured population was then re-stained with anti-CD4-PE-Cy7, anti-CD25-APC, and anti-CD134-FITC monoclonal antibodies; and antigen-specific CD4$^+$CD25$^+$CD134$^+$ cells were isolated by FACS cell sorting. The purity of the sorted cells was at least 95%, which was determined by taking an aliquot of the sorted subset and re-analysing it by flow cytometry to determining the percentage of cells remain within the original sorting gate. An aliquot of these isolated CD4$^+$CD25$^+$CD134$^+$ CMV-P1-specific Treg were expanded in culture supplemented with 10 U IL-2 (data not shown). An aliquot of the isolated CD4$^+$CD25$^+$CD134$^+$ CMV-P1-specific Treg were stored in TRIZOL at −70° C. for use in real-time PCR studies.

Determining Foxp3 Expression on the CD4$^+$CD25$^+$CD134$^+$ Cells from the Cultured Populations Following culturing with antigen, an aliquot of each cultured population was stained to determine the Foxp3 expression of the CD4$^+$CD25$^+$CD134$^+$ cells in a separate staining experiment.

Results and Discussion

Figure 9:
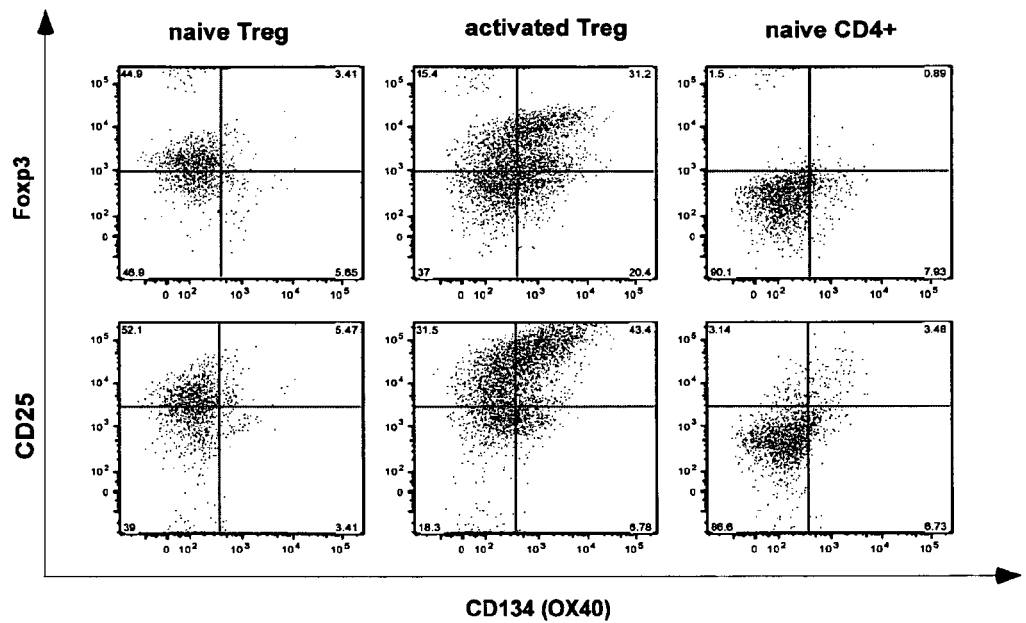
FIG. 9 provides FACS analysis data of sorted naïve Treg activated Treg or naïve CD4$^+$ cell populations following stimulation with CMV-P1 peptide antigen showing (top) plots of Foxp3, CD25 and CD134 expression, and (bottom) histograms of Foxp3 expression of the antigen-specific CD4$^+$CD25$^+$CD134$^{30}$ Treg subset of each population.
Figure 9:
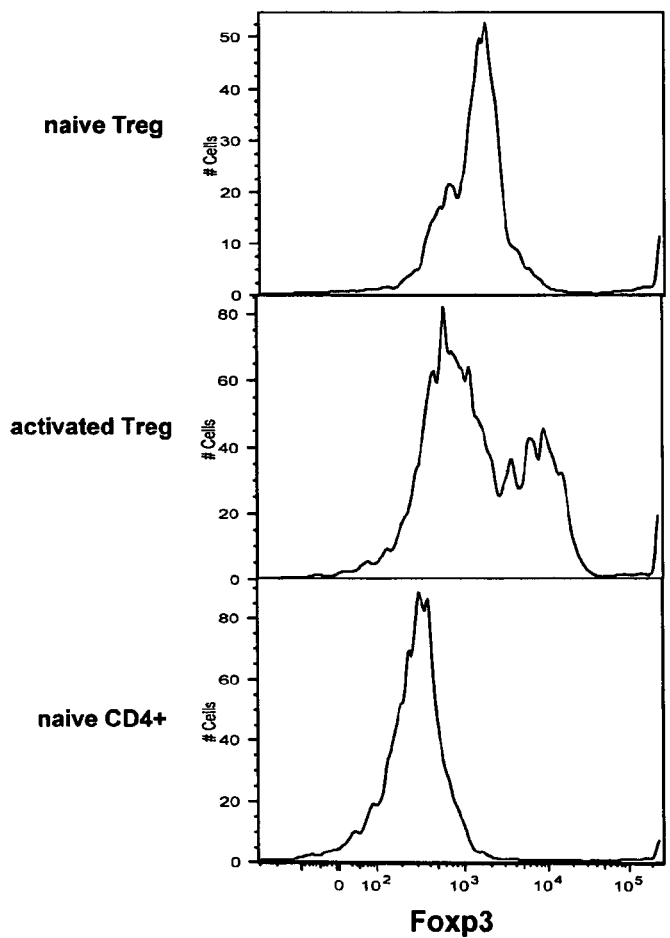
Figure 10:
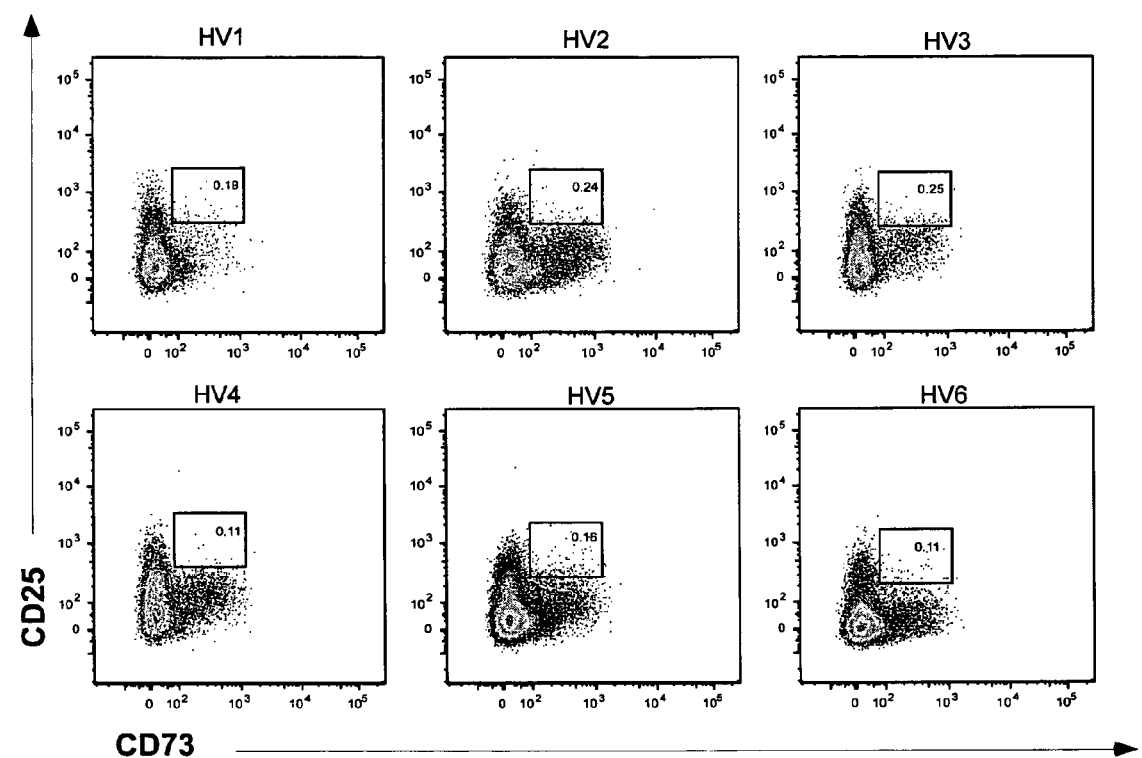
FIG. 10 provides FACS analysis plots of PBMCs from six different healthy donors (HV1 to HV6) showing CD25 and CD73 expression.

Sorted populations of naïve Treg (CD4+CD25$^+$CD127$^{lo}$CD45RO$^-$), activated Treg (CD4+CD25$^+$CD127$^{lo}$CD45RO$^+$) and naïve CD4+CD25 T cells were cultured with CMV-P1 antigen, following which, CD4$^+$CD25$^+$CD134$^+$ antigen-specific Treg could be identified from all three populations. The naïve Treg and activated Treg populations had higher levels of Foxp3 expression after culturing with antigen than the naïve T cell population cultured in the same conditions, as shown in FIG. 9 (top panel). CD25 expression was lower (less than 7%) in the cultured naïve T cell population compared to the cultured naïve Treg and activated Treg populations, where 50% of the cells express CD25 (bottom panel). The histograms in FIG. 9 (bottom) show Foxp3 expression on CD4$^+$CD25$^+$CD134$^+$ cells from the populations of naïve Treg activated Treg and naïve T cell populations following culturing with antigen.

The results show that a pure population of antigen-specific Treg can be isolated by initially FACS sorting cells to isolate naïve Treg (CD4+CD25$^+$CD127$^{lo}$CD45RO$^-$) into a pure population, and then stimulating these cells with antigen in vitro, before re-sorting these cells to isolate antigen-specific Treg (CD4$^+$CD25$^+$CD134$^+$).

Further, a pure population of antigen-specific Treg can be isolated by initially FACS sorting cells to isolate activated Treg (CD4+CD25$^+$CD45RO$^+$CD127$^{lo}$) into a pure population, and then stimulating these cells with antigen in vitro, before re-sorting these cells to isolate antigen-specific Treg (CD4$^+$CD25$^+$CD134$^+$).

Example 12

Expression of CD73 on CD4$^+$CD25$^+$CD127lo Treg

CD73 has been reported to be a Treg marker in mice (18), and it was accordingly investigated in the present system.

Materials and Methods

Peripheral blood was collected from six different healthy donors (HV1 to HV6), and PBMCs were isolated. The PBMCs were stained with a combination of anti-CD3-PercpCy5.r, anti-CD4-PE-Cy7, anti-CD25-APC, anti-CD73-PE (Becton-Dickinson) and anti-CD127-Pacific-Blue and analysed by FACS as described above.

Results and Discussion

Figure 11:
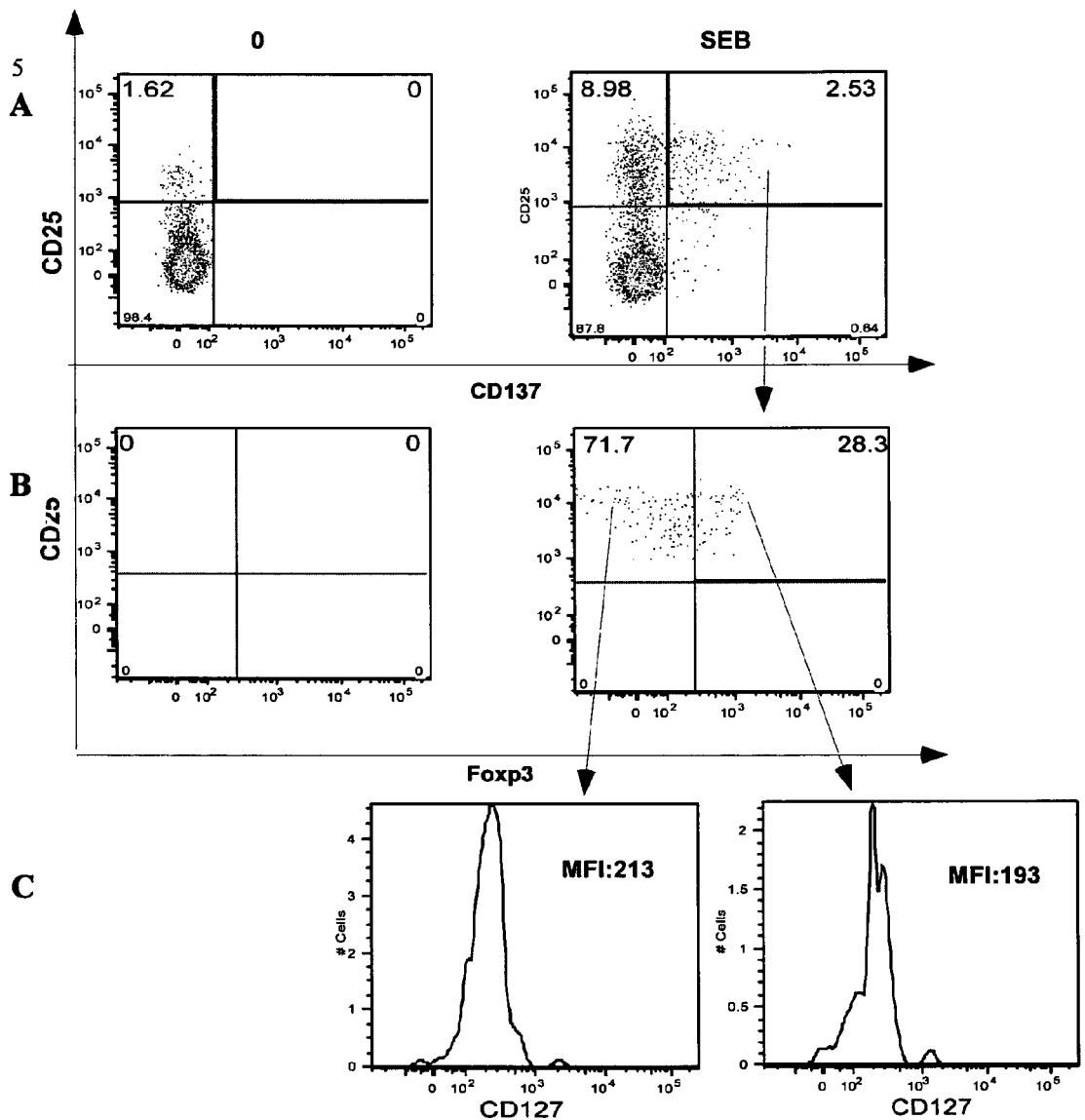
FIG. 11 provides FACS analysis plots of Foxp3 and CD127 expression on CD8$^+$CD25$^+$CD137$^+$ antigen-specific Treg in whole blood following in vitro stimulation without (0) or with SEB for 40 hr. (A) CD137 expression and CD25 expression on CD8$^+$ cells. (B) Foxp3 expression on the CD8$^+$CD25$^+$CD137$^+$ subsets of (A). (C) CD127 expression of the CD8$^+$CD25$^+$CD137$^+$Foxp3$^-$ (left) and CD8$^+$CD25$^+$CD137$^+$Foxp3$^+$ (right) cells.

FIG. 11 shows CD25 and CD73 expression on CD3+CD4$^+$ T cells. The results indicate that a very low percentage of cells were CD25$^+$CD73$^+$, indicating that CD73 may be a less effective marker for Treg in humans as it was not co-expressed with a significant subset of CD25$^+$ cells.

Example 13

Identification and Isolation of CD8+CD25+CD137+ Foxp3+CD127$^{lo}$ Antigen-Specific Treg from Whole Blood Stimulation with a defined viral antigen such as Hepatitis C virus or Influenza virus specific peptides can lead to the expansion of two different CD8+ T cell populations: CD8+ Foxp3−memory/effector T cells as well as CD8+Foxp3+ Treg (35). Although the biological role of CD8+ Treg is not well understood, there is increasing evidence that different subsets of CD8+ T cells possess a regulatory ability in humans and mice (36-42). Pre-existing CD8+Foxp3+ Treg may be recruited to the sites of active immune responses, where they may suppress antigen-specific immune responses.

In this example, anti-CD8, anti-CD25, and anti-CD137 antibodies, as well as one or more of anti-Foxp3 and anti-CD127 antibodies, were investigated for use in identifying CD8+ antigen-specific Treg.

Materials and Methods

In Vitro Stimulation

Whole blood from a healthy donor was stimulated in vitro with no antigen or SEB and cultured for 40 hours as described in Example 1 and 2.

Identification of CD8+CD25+CD127$^{lo}$CD137+Foxp3+ Antigen-Specific Treg

An aliquot of cultured whole blood cells was stained with a combination of monoclonal antibodies comprising anti-CD3, anti-CD8, anti-CD25, anti-CD127, anti-CD137 and anti-Foxp3 antibodies. Cell staining was analysed on a three-laser LSR II flow cytometer (Becton-Dickinson). A minimum of 100,000 events, were collected and analysis was performed using FlowJo software. Antigen-specific Treg were gated as CD3+CD8+CD25+CD137+Foxp3+. The expression of CD127 was examined on both the CD8+CD25+CD137+Foxp3+ and CD8+CD25+CD137+Foxp3+ cell populations.

Isolation of CD8+CD25+CD127$^{lo}$CD137+ Viable Antigen-Specific Treg

The remaining cultured whole blood cells were stained with a combination of monoclonal antibodies, specifically, anti-CD8, anti-CD25, anti-CD127 and anti-CD137. CD8+ CD25+CD127$^{lo}$CD137+ cells were sorted on a three-laser LSR II flow cytometer (Becton-Dickinson), and stored in TRIZOL at −70° C. for further studies.

Results and Discussion

The use of anti-CD137 monoclonal antibody together with anti-CD25 and anti-Foxp3 monoclonal antibodies within the CD8+ T cell population allowed an accurate identification of CD8+ antigen-specific Treg after in vitro stimulation with antigen. FIG. 11 shows cultured cells stained with CD8, CD25, CD137 and Foxp3. FIG. 11A demonstrates CD137 expression and CD25 expression on CD8+ cells cultured with or without SEB in whole blood. FIG. 11B shows the Foxp3 expression on the CD8+CD25+CD137+ subsets of the in vitro stimulated cells. About 28% of the CD8+CD25+CD137+ cells stimulated with SEB express Foxp3, while cells that were not in vitro stimulated did not have a CD8+CD25+CD137+ population that expressed Foxp3.

As shown in FIG. 11C, the CD8+CD25+CD137+Foxp3+ cells had lower CD127 expression (MFI:193) than the CD8+ CD25+CD137+Foxp3− cells (MFI:213), which is consistent with previous results showing that CD8+CD25+Foxp3+ cells express CD127 at lower levels than effector cells (18). Accordingly, one or more of Foxp3 or CD127, wherein CD127 expression is CD127$^{lo}$, are appropriate markers to detect antigen-specific CD8+Treg in combination with CD8, CD25 and CD137.

Prophetic Example 1

In Vitro Expansion of Antigen-Specific Treg

Materials and Methods

Ex Vivo Expansion of Antigen-Specific Treg

The isolated antigen-specific CD4+CD25+CD134+ Treg can be expanded ex vivo or in vitro using high doses of IL-2 according to two different protocols described below:

(i) Isolated Treg can be expanded as previously described (43,44). In particular, isolated antigen-specific Treg will be placed into 96-well flat-bottom plates with $1.5 \times 10^4$ irradiated (70 Gy) CD32+ L cells (L929-derived murine Ltk cell line stably transfected with human FcγRII (CD32) (45). Cultures will be in 200 μL RPMI media (RPMI 1640 with 10% fetal calf serum (FCS) (Gibco BRL, Karlsruhe, Germany), 2 mM glutamine, 50 U/mL penicillin, 50 □g/mL streptomycin, (all Gibco BRL)) with 10 □g/mL target antigen, 100 ng/mL anti-CD28 antibody (CD28.2; BD Biosciences), and 100-300 U/mL IL-2 (rhIL-2; Proleukin, Chiron, Amsterdam, the Netherlands). After 5 to 6 days, cells will be harvested, and $1 \times 10^5$ Treg will be co-cultured with $8 \times 10^4$ CD32+ L cells in 500 μL RPMI supplemented with anti-CD28, antigen and IL-2 in 24-well plates. Cultures will be supplemented with 200 μL RPMI/IL-2 after 4 days and split onto fresh CD32+ L cells once per week.

(ii) Beads are prepared as previously described (46) but modified as follows: 200 million epoxy-activated magnetic beads, 4.5 μm in diameter (Dynal Biotech, Lake Success, N.Y., United States of America) will be coated with a total of 35 μg of anti-CD28 mAb overnight at 4° C. in a 0.1 M borate buffer at pH 7.2. Excess uncoated mAb will be removed by three 10-min washes and one overnight wash at 4° C. in Bead Wash Buffer (PBS, 3% human AB serum, 0.5 M EDTA, and 1% sodium azide). Isolated antigen-specific Treg will be cultured in 96-well U-bottom plates by adding prepared anti-CD28 beads at a ratio of 4 beads per cell to $2 \times 10^4$ Treg for the first week, and at a 1:1 ratio with $5 \times 10^5$ cells per well in 24-well plates thereafter. Cells will be cultured in RPMI with 100-300 U/mL IL-2, fed with RPMI/IL-2 after 4 days, and re-stimulated with fresh beads weekly. Treg expansion will be determined by counting trypan blue-negative aliquots in approximately weekly intervals.

Determining Suppressive Function

The function of these cells can be tested in vitro by using a suppression assay as reported previously (17), or variations thereof, or by using real-time PCR to investigate expression levels of genes associated with suppressive function as described above, and the stability of the Treg phenotype can be checked as described above.

Determining TCR Specificity

The TCR repertoire of antigen-specific CD4+CD25+ CD134+ Treg following stimulation with a specific antigen can be studied. In some cases, it may be useful to compare the TCR repertoire of antigen-specific Treg with those of naïve Treg and activated Treg as well as those of effector and memory CD4+ T cell subsets. The protocol of TCR studies will be as follows: Sorted cells (eg antigen-specific Treg) will be stored in Trizol at −70° C. until RNA extraction. On thawing of samples, 200 μL of chloroform (Sigma-Aldrich Co.), will be added and mixed thoroughly for 15 seconds, incubated for 3 minutes at room temperature, then centrifuged at 12000 g for 15 minutes. To precipitate RNA, 10 μg of glycogen (Roche) and an equal original volume of 2-propanol will be added and incubated on ice for 10 minutes and the RNA will be pelleted by centrifugation at 12000 g for 10 minutes, washed with 1 mL cold 70% ethanol, centrifuged at 7600 g for 5 minutes then dried for 10 minutes at 37° C. RNA will be then resuspended in 20 µl DEPC water pre-heated to 60° C. and incubated at 60° C. for a further 5 minutes. Samples will be cooled on ice prior to storing at −70° C.

RNA samples will be used for further experiments to amplify TCR β-chain template. First-strand cDNA template will be generated from a reaction mix containing 1.2 µg hexamer random primers (Invitrogen), Expand RTase buffer (Roche), 10 mM DTT (Roche), 40 U Protector RNAse Inhibitor (Roche), 2.5 mM dNTP (Invitrogen) and 1 µL Expand reverse transcriptase (Roche) pre-diluted at 2 µL in a separate aliquot of 2× Expand RTase buffer, 200 µM DTT in final volume of 20 µL. Template will be incubated for 60 minutes at 42° C. before storage at −20° C. Gene specific TCR β-chain amplification will be performed using BV3 and reverse BVCR primers at 500 nM, Expand Hi-Fidelity PCR buffer, 250 nM dNTPs and 3 U Expand Hi-Fidelity DNA Polymerase (Roche). PCR conditions will be 94° C. for 2 minutes, 35 cycles at 94° C. for 15 seconds, 54° C. for 30 seconds and 72° C. for 1 minute and final extension time of 72° C. for 10 minutes. Unbiased TRBV first-strand cDNA template will be generated as previously described (47). Product amplified from sorted cells will be visualised on a 2% agarose gel and purified. Purified product will be ligated into either a TOPO-TA cloning vector (Invitrogen) and transformed into chemically competent TOP10 *E. coli* (GIMR), or ligated into a pGEM-Teasy vector (Promega) and transformed into *E. coli* DH5α (VRC). Colonies will be selected by blue/white screening and carriage of inserts will be confirmed by PCR amplification of inserts using generic M13 primers. A minimum of 50 clones will be sequenced per sample using BigDye v3.1 sequencing reaction on an ABI 3730×1 capillary sequencing machine. Sequences will be aligned using Sequencher (Gene Codes Corporation) and clonotype identity determined using alignments confirmed using the Immunogenetics online sequence analysis algorithm (IMGT, the international ImMunoGeneTics Information System® http://imgt.cines.fr (Initiator and coordinator: Marie-Paule Lefranc, Montpellier, France)). To determine dataset similarity, population overlap will be assessed using the Morisita-Horn similarity index (C-MH) as compared by permutation analysis. Data will be analysed using expertise in biostatistics. The data generated can also provide information regarding the origin of antigen-specific Treg (eg whether they derive from peripheral memory or effector T cell subsets).

Results and Discussion

Isolation and expansion of antigen-specific Treg ex vivo or in vitro may provide the means to overcome the problems associated with the use of antigen-specific Treg in the clinic, namely, that peripheral Treg are present in low numbers in the circulation and have broad and poorly defined antigen specificity. Antigen-specific Treg specific for a target antigen can be identified, and induced to expand ex vivo, and accordingly, Treg of the desired antigen specificity can be generated as required. These expanded antigen-specific Treg can be re-infused into subjects where Treg cell-therapy may be beneficial.

Although a preferred embodiment of the apparatus of the present invention has been described in the foregoing detailed description, it will be understood that the invention is not limited to the embodiment disclosed, but is capable of numerous rearrangements, modifications and substitutions without departing from the scope of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

REFERENCES

1. Shevach. 2006. From vanilla to 28 flavors: multiple varieties of T regulatory cells. *Immunity.* 25:195-201.
2. Roncarolo et al. 2007. Regulatory T-cell immunotherapy for tolerance to self antigens and alloantigens in humans. *Nat Rev Immunol.* 7:585-598.
3. Groux et al. 1997. A CD4+ T-cell subset inhibits antigen-specific T-cell responses and prevents colitis. *Nature.* 389:737-742.
4. Walker et al. 2003. Induction of FoxP3 and acquisition of T regulatory activity by stimulated human CD4+CD25− T cells. *J Clin Invest.* 112:1437-1443.
5. Hori et al. 2002. Specificity requirements for selection and effector functions of CD25+4+ regulatory T cells in anti-myelin basic protein T cell receptor transgenic mice. *Proc Natl Acad Sci USA.* 99:8213-8218.
6. Scalapino et al. 2006. Suppression of disease in New Zealand Black/New Zealand White lupus-prone mice by adoptive transfer of ex vivo expanded regulatory T cells. *J Immunol.* 177:1451-1459.
7. Tang et al. 2004. In vitro-expanded antigen-specific regulatory T cells suppress autoimmune diabetes. *J Exp Med.* 199:1455-1465.
8. Tarbell et al. 2004. CD25+ CD4+ T cells, expanded with dendritic cells presenting a single autoantigenic peptide, suppress autoimmune diabetes. *J Exp Med.* 199:1467-1477.
9. Baecher-Allan and Hafler. 2006. Human regulatory T cells and their role in autoimmune disease. *Immunol Rev.* 212:203-216.
10. Bacchetta et al. 2006. Defective regulatory and effector T cell functions in patients with FOXP3 mutations. *J Clin Invest.* 116:1713-1722.
11. Marangoni et al. 2007. WASP regulates suppressor activity of human and murine CD4(+)CD25(+)FOXP3(+) natural regulatory T cells. *J Exp Med.* 204:369-380.
12. Kriegel et al. 2004. Defective suppressor function of human CD4+ CD25+ regulatory T cells in autoimmune polyglandular syndrome type II. *J Exp Med.* 199:1285-1291.
13. Bleesing et al. 2001. Immunophenotypic profiles in families with autoimmune lymphoproliferative syndrome. *Blood.* 98:2466-2473.
14. Miura et al. 2004. Association of Foxp3 regulatory gene expression with graft-versus-host disease. *Blood.* 104:2187-2193.
15. Rezvani et al. 2006. High donor FOXP3-positive regulatory T-cell (Treg) content is associated with a low risk of GVHD following HLA-matched allogeneic SCT. *Blood.* 108:1291-1297.

16. Zorn et al. 2005. Reduced frequency of FOXP3+ CD4+ CD25+ regulatory T cells in patients with chronic graft-versus-host disease. *Blood.* 106:2903-2911.
17. Seddiki et al. 2006. Expression of interleukin (IL)-2 and IL-7 receptors discriminates between human regulatory and activated T cells. *J Exp Med.* 203:1693-1700.
18. Deaglio et al. 2007. Adenosine generation catalyzed by CD39 and CD73 expressed on regulatory T cells mediates immune suppression. *J Exp Med.* 204:1257
19. Borsellino et al. 2007. Expression of ectonucleotidase CD39 by Foxp3 Treg cells: hydrolysis of extracellular ATP and immune suppression. *Blood,* 110:1225
20. Rouse. 2007. Regulatory T cells in Health and Disease. *J Intern Med.* 262:78-95
21. Piersmaa et al. 2008. Tumor-specific regulatory T cells in cancer patients. *Hum Immunology,* 69:241-249
22. Zaunders et al. 2004. Identification of circulating antigen-specific CD4+ T lymphocytes with a CCR5+, cytotoxic phenotype in an HIV-1 long-term nonprogressor and in CMV infection. *Blood* 103:2238.
23. Harcourt et al. 2006. Identification of key peptide-specific CD4+ T cell responses to human cytomegalovirus: implications for tracking antiviral populations. *Clin Exp Immunol.* 146:203-210.
24. Li Pira et al. 2004. Recognition of CMV pp65 protein antigen by human CD4 T-cell lines induced with an immunodominant peptide pool. *Hum Immunol.* 65:537-543.
25. Hori et al. 2003. Control of regulatory T cell development by the transcription factor Foxp3. *Science,* 299:1057-1061
26. Fontenot et al. 2003. Foxp3 programs the development and function of CD4+CD25+ regulatory T cells. *Nat. Immunol.* 4:330-336
27. Khattri et al. 2003. An essential role for Scurfin in CD4+ CD25+ T regulatory cells. *Nat. Immunol.* 4:337-342
28. Marie et al. 2005. *J. Exp. Med.* 2011061-1067
29. Cousins et al. 2002. *J Immunol.* 169: 2498-2506
30. Sakaguchi et al. 2008. Regulatory T cells and immune tolerance. *Cell.* 2008 133(5):775-87.
31. Zheng et al. 2004. *J. Immunol.* 172, 5213-5221
32. Seddiki et al. 2006. *Blood,* 107:2830
33. Koenen et al. 2008. *Blood* 112:2340
34. Fehervari et al. 2006. *Trends in Immunol.,* 27:109
35. Billerbeck et al. 2007. Parallel expansion of human virus-specific FoxP3– effector memory and de novo-generated FoxP3+ regulatory CD8+ T cells upon antigen recognition in vitro. *J Immunol.* 179:1039-1048.
36. Bisikirska et al. 2005. TCR stimulation with modified anti-CD3 mAb expands CD8+ T cell population and induces CD8+CD25+ Tregs. *J Clin Invest.* 115:2904-2913.
37. Cosmi et al. 2003. Human CD8+CD25+ thymocytes share phenotypic and functional features with CD4+ CD25+ regulatory thymocytes. *Blood.* 102:4107-4114.
38. Dittmer et al. 2004. Functional impairment of CD8(+) T cells by regulatory T cells during persistent retroviral infection. *Immunity.* 20:293-303.
39. Endharti et al. 2005. Cutting edge: CD8+CD122+ regulatory T cells produce IL-10 to suppress IFN-gamma production and proliferation of CD8+ T cells. *J Immunol.* 175:7093-7097.
40. Gilliet et al. 2002. Generation of human CD8 T regulatory cells by CD40 ligand-activated plasmacytoid dendritic cells. *J Exp Med.* 195:695-704.
41. Shevach. 2006. From vanilla to 28 flavors: multiple varieties of T regulatory cells. *Immunity.* 25:195-201.
42. Zheng et al. 2004. CD4+ and CD8+ regulatory T cells generated ex vivo with IL-2 and TGF-beta suppress a stimulatory graft-versus-host disease with a lupus-like syndrome. *J Immunol.* 172:1531-1539.
43. Hoffmann et al. 2006, *Blood.* 108, 4260-7
44. Hoffmann et al. 2004, *Blood.* 104, 895-903
45. Peltz et al. 1988, *J Immunol.* 141, 1891-6
46. Maus et al. 2004. *J Immunol.* 172:6675-83
47. Douek et al. 2002. *J Immunol.* 168:3099-104
48. Vu et al. 2007. OX40 costimulation turns off Foxp3 Tregs. *Blood.* 110:2501.

The invention claimed is:

1. A method of identifying a target-antigen-specific regulatory T cell (Treg) from a subject, the method comprising the following steps:
   (i) obtaining a suitable lymphocyte-containing sample from the subject;
   (ii) combining a soluble target antigen with the lymphocyte-containing sample in vitro;
   (iii) culturing the lymphocyte-containing sample and said soluble target antigen in vitro for a period of time of about 24 to 96 hours and before the target-antigen-specific Treg have divided; and thereafter,
   (iv) quantifying the target-antigen-specific Treg by detecting co-expression in a cell of each of cell markers CD4, CD25, CD134 and CD39 in the cultured sample;
   wherein detecting the co-expression of each of the cell markers identifies the target-antigen-specific Treg that specifically recognizes and responds to said target antigen.

2. The method of claim 1 wherein the cell markers detected are CD4, CD25, CD134 and CD39 and CD127.

3. The method of claim 1 wherein the culturing step is performed in vitro for a period of time of about 40 to 44 hours.

4. The method of claim 1 wherein the culturing step is performed in vitro for a period of time of about 72 hours.

5. A method of isolating target-antigen-specific Treg from a subject comprising isolating the cells identified according to the method of claim 1.

6. The method of claim 5, wherein the culturing step is performed in vitro for a period of time of about 72 hours.

7. The method of claim 5, wherein the culturing step is performed in vitro for a period of time of about 40 to 44 hours.

8. A method of providing an expanded population of target-antigen-specific Treg, wherein the method comprises expanding in vitro the population of target-antigen-specific Treg isolated according to the method of claim 5.

9. The method of claim 1, wherein the lymphocyte-containing sample is a whole blood sample.

10. The method of claim 1, wherein the lymphocyte-containing sample is a purified peripheral blood mononuclear cell sample.

11. The method of claim 1, wherein the subject is human.

12. The method of claim 1, wherein step (iv) further comprises detecting co-expression of one or more cell markers selected from the group of Treg cell markers consisting of CD127, CTLA-4 and Foxp3.

13. A method of isolating a target-antigen-specific regulatory T cell (Treg) from a subject, the method comprising the following steps:
   (i) obtaining a suitable lymphocyte-containing sample from the subject;
   (ii) isolating naïve Treg or activated Treg expressing one or more cell markers selected from the group consisting of CD39, CD45RA, CD45RO, CD73, CD127 and CTLA-4 from said suitable lymphocyte-containing sample from the subject;
   (iii) combining a soluble target antigen with said isolated naïve or activated Treg in vitro;

(iv) culturing said isolated naïve or activated Treg and said soluble target antigen in vitro for a period of time of about 24 to 96 hours and before the target antigen specific Treg have divided; and thereafter;

(v) isolating the target-antigen-specific Treg by detecting co-expression in a cell of each of the cell markers CD4, CD25, CD134 and CD39 and isolating cells detected co-expressing in a cell each cell marker CD4, CD25, CD134 and CD39 by cell sorting with monoclonal antibodies specific to each of CD4, CD25, CD134 and CD39, wherein detecting the co-expression of each of the cell markers identifies the target-antigen-specific Treg that specifically recognizes and responds to said target antigen.

14. The method claim 13, wherein step (v) comprises isolating $CD4^+CD25^+CD134^+CD39^+$ cells that also co-express one or more cell markers selected from the group of Treg cell markers consisting of CD45RO, CD127, CTLA-4 and Foxp3.

15. The method of claim 13, wherein the culturing step is performed in vitro for a period of time of about 72 hours.

16. The method of claim 13, wherein culturing step is performed in vitro for a period of time of about 40 to 44 hours.

17. A method of providing an expanded population of target-antigen-specific Treg, wherein the method comprises expanding in vitro the population of target-antigen-specific Treg isolated according to the method of claim 13.

18. The method of claim 17, wherein the step of expanding the population of antigen-specific Treg comprises culturing in the presence of interleukin-2 (IL-2).

* * * * *